US011857683B2

(12) United States Patent
Shah et al.

(10) Patent No.: US 11,857,683 B2
(45) Date of Patent: Jan. 2, 2024

(54) STABILIZATION OF PHENOBARBITAL SODIUM FOR INJECTION

(71) Applicant: SUN PHARMA ADVANCED RESEARCH COMPANY LIMITED, Maharashtra (IN)

(72) Inventors: Malay Shah, Vadodara (IN); Bhushan Borole, Jalgaon (IN); Ravi Patel, Anand (IN); Ajay Jaysingh Khopade, Vadodara (IN)

(73) Assignee: SUN PHARMA ADVANCED RESEARCH COMPANY LIMITED, Mumbai (IN)

( * ) Notice: Subject to any disclaimer, the term of this patent is extended or adjusted under 35 U.S.C. 154(b) by 0 days.

(21) Appl. No.: 17/715,491

(22) Filed: Apr. 7, 2022

(65) Prior Publication Data
US 2023/0031957 A1   Feb. 2, 2023

Related U.S. Application Data

(60) Provisional application No. 63/319,918, filed on Mar. 15, 2022.

(30) Foreign Application Priority Data

Jul. 7, 2021   (IN) .............................. 202121030559

(51) Int. Cl.
| *A61K 9/19* | (2006.01) |
| *A61P 25/08* | (2006.01) |
| *A61K 9/08* | (2006.01) |
| *A61K 31/515* | (2006.01) |
| *A61K 47/10* | (2017.01) |

(52) U.S. Cl.
CPC .................. *A61K 9/19* (2013.01); *A61K 9/08* (2013.01); *A61K 31/515* (2013.01); *A61K 47/10* (2013.01); *A61P 25/08* (2018.01)

(58) Field of Classification Search
None
See application file for complete search history.

(56) References Cited

U.S. PATENT DOCUMENTS

| 9,901,576 B2 | 2/2018 | Parker et al. | |
| 2021/0085608 A1* | 3/2021 | Chodavarapu | ....... A61K 9/0019 |

FOREIGN PATENT DOCUMENTS

AU         495261 B2      3/1977

OTHER PUBLICATIONS

Gupta et al (Effect of Ethanol, Glycerol, and Propylene Glycol on the Stability of Phenobarbital Sodium. Journal of Pharmaceutical Sciences. vol. 73, No. 11, Nov. 1984. p. 1661-1662. (Year: 1984).*
Nobelbar label with English translation, Nov. 2020, 10 pages.
Kou Kawada et al., A Clinical Trial Assessing the Efficacy and Safety of a New Injectable Formula of Sodium Phenobarbital Containing No Additives for the Treatment of Neonatal Seizures, Jpn J Clin Pharmacol Ther 42(4), Jul. 2011, pp. 205-209.
Kou Kawada, Overview of the Clinical Trial Leading to Approval of "Nobelbar" and Package Insert Information, Neonatal Care vol. 22, No. 7, 14 pages, (2009).
Nobelbar, Deliberation Results Report, Sep. 16, 2008, 86 pages.
International Search Report, Application No. PCT/IB2022/056290, dated Oct. 20, 2022.
J.C. Kossmann et al., Pharmacocinétique du phénobarbital injectable chez le premature—Etude à partir d'une nouvelle forme lyophilisée (Pharmacokinetics of injectable phenobarbital in the premature infant—Study of a new lyophilized form), Arch. Fr. Ped., vol. 42, No. 4, Apr. 1985, pp. 317-320 (English abstract retrieved from the Internet at http://www.ncbi.nlm.nih.gov/pubmed/4004495 ) (partial machine translation obtained).
V. Das Gupta, "Effect of Ethanol, Glycerol, and Propylene Glycol on the Stability of Phenobarbital Sodium", J. Pharm Sci., vol. 73, No. 11, Nov. 1984, pp. 1661-1662.
Certificate of Analysis, Phenobarbital Sodium USP, Harman Finochem Ltd., Date of Manufacturing Dec. 2015, 1 page.
Certificate of Analysis, Phenobarbital Sodium USP, Harman Finochem Ltd., Date of Manufacturing May 2020, 1 page.
Phenobarbital sodium, Orphan drug designations and approvals, https://www.accessdata.fda.gov/scripts/opdlisting/oopd/detailedIndex.cfm?cfgridkey=703819, accessed Apr. 16, 2023 (2 pgs).
Sharpe C., et al. "Levetiracetam Versus Phenobarbital for Neonatal Seizures: A Randomized Controlled Trial," Pediatrics. Jun. 2020; 145(6):e20193182. doi: 10.1542/peds.2019-3182 (12 pgs).
Sun Pharma Launches SEZABY™ (phenobarbital sodium) in the U.S. for Treatment of Neonatal Seizures, Jan. 25, 2023 (3 pgs).

* cited by examiner

*Primary Examiner* — Jake M Vu
(74) *Attorney, Agent, or Firm* — Foley & Lardner LLP

(57) ABSTRACT

The present invention relates to a lyophilized pharmaceutical composition of hydrolytically unstable pharmaceutical compounds, such as phenobarbital or salts thereof. The present invention also relates to an aqueous solution for injection of phenobarbital or salts thereof that is reconstituted from the lyophilized pharmaceutical composition. The pharmaceutical compositions of the present disclosure have an ethanol content in the range from about 5000 ppm to about 70000 ppm. The composition of the present disclosure, in certain embodiments, is stable following two years of storage, wherein the total impurities do not exceed 0.5%. The pharmaceutical compositions of the present disclosure may be used for the treatment of neonatal seizures.

25 Claims, No Drawings

STABILIZATION OF PHENOBARBITAL SODIUM FOR INJECTION

CROSS REFERENCE TO PRIOR APPLICATION

This application claims priority to Indian Patent Application No. 202121030559 (filed on Jul. 7, 2021) and U.S. Provisional Patent Application No. 63/319,918 (filed on Mar. 15, 2022), which are all hereby incorporated by reference in their entirety.

FIELD OF THE INVENTION

The present invention relates to a lyophilized pharmaceutical composition of hydrolytically unstable pharmaceutical compounds, such as phenobarbital or salts thereof. The present invention also relates to an aqueous solution for injection of phenobarbital or salts thereof that is reconstituted from the lyophilized pharmaceutical composition. The pharmaceutical compositions of the present disclosure have an ethanol content in the range from about 5000 ppm to about 70000 ppm. The composition of the present disclosure, in certain embodiments, is stable following two years of storage, wherein the total impurities do not exceed 0.5%. The pharmaceutical compositions of the present disclosure may be used for the treatment of neonatal seizures.

BACKGROUND OF THE INVENTION

Phenobarbital is an anti-epileptic drug which has been used for many years in the treatment of neonatal seizures. One of the problems associated with a phenobarbital composition, however, is its instability due to hydrolysis, which causes it to possess a higher level of impurities. While the compound is freely soluble in water, with solubility reported to be as high as 333 mg/ml to 1 g/ml, the presence of hydroxyl ions from the water in the composition results in a hydrolysis pathway that can destroy the phenobarbital ring complex. This destruction results in the possible formation of impurities including harmful degradants or precipitates.

One known method of improving the stability of phenobarbital sodium involves the use of a lower pH and the use of a mixture of water and generic solvents such as alcohol, propylene glycol, glycerin, benzyl alcohol, or polyethylene glycol. Currently, marketed compositions of phenobarbital sodium injections contain benzyl alcohol, alcohol, and propylene glycol, which pose a higher toxicity risk to neonates and therefore present a potential safety risk when used in the treatment of neonatal seizures. Nevertheless, neonatologists have no choice but to give benzyl alcohol-, alcohol-, and propylene glycol-containing compositions to neonates. The use of a combination of various cosolvents at a higher concentrations also causes a higher osmolality (>500 mOsm) of the product. This is of particular concern for preterm infants, who are particularly vulnerable to the adverse effects of intravenous administration of hypertonic substances, as their infusions have been associated with increased risk of intraventricular hemorrhage, hepatic necrosis and necrotizing enterocolitis. Studies have shown that hyperosmolality and metabolic acidosis, then renal dysfunction and finally acute renal failure and clinical deterioration are major effects of increasing doses and serum concentrations of propylene glycol in neonates. In addition several case reports of intoxication have pointed out the potential CNS (lethargy, coma, seizures) or local vascular affects (including hemolysis) most probably associated to higher plasma levels of propylene glycol and hyperosmolality following acute toxicity.

Propylene glycol is an example of a compound used commercially as a diluent or stabilizer in some extremely hypertonic preparations for intravenous use, including phenytoin, phenobarbital, diazepam, digoxine, and multivitamin solutions. Although it is considered to be a relatively safe substance, serum hyperosmolality and other harmful effects to newborns and infants have been reported, including secondary to transdermal absorption of propylene glycol from topical pharmaceutical preparations. In addition, the toxicity of propylene glycol to newborns and infants may be particularly acute because infants and newborns may have a delayed development of mechanisms to eliminate propylene glycol from their systems. All of these issues with propylene glycol has thus encouraged the search for alternatives to propylene glycol for use as a diluent for substances for intravenous use in neonates.

U.S. Patent Application Publication No. 20210085608 relates to phenobarbital sodium formulations and lyophilization. According to this publication, lyophilization may result to the stability in a phenobarbital sodium formulation. However, this publication fails to disclose or suggest the role that ethanol may play in the stability of a phenobarbital formulation.

U.S. Pat. No. 9,901,576 relates to phenobarbital formulations. However, the examples of this patent contains higher amount ethanol for the stability. According to regulatory guidelines (for example European Medicines Agency guidance and The International Council for Harmonisation of Technical Requirements for Pharmaceuticals for Human Use), the formulations having the solvent amount of over 50000 ppm are unsuitable for use in neonates.

SUMMARY OF THE INVENTION

The present inventors have developed stable pharmaceutical compositions of the hydrolytically unstable drug phenobarbital or salts thereof. The pharmaceutical compositions of the present disclosure provides stability over a lengthy shelf life, as measured by the amount of total impurities formed over time and that does not generate any significant amount of impurities during extended storage. The present inventors have also observed that the presence of higher levels of alcohol alone is not sufficient to control the level of impurities. Thus, embodiments of the present disclosure relate to the pharmaceutical compositions of phenobarbital or salts thereof and methods of preparing the same by utilizing a combination of a certain level of alcohol and lyophilization.

In the first aspect, the present disclosure relates to a pharmaceutical composition of phenobarbital or salts thereof that has been reconstituted from a lyophilized pharmaceutical composition of phenobarbital or salts thereof, wherein the amount of total impurities in the pharmaceutical composition does not exceed 0.2% following 12 hours of storage at 20-25° C. or 36 hours of storage at 2-8° C.

In the second aspect, the present disclosure relates to a pharmaceutical composition of phenobarbital or salts thereof, wherein the pharmaceutical composition has an alcohol content in the range from about 5000 ppm to 66000 ppm or alternatively from about 5000 ppm to 70000 ppm.

In the third aspect, the present disclosure relates to a lyophilized pharmaceutical composition of phenobarbital or salts thereof, wherein the composition has an alcohol content in the range from about 5000 ppm to about 66000 ppm or alternatively from about 5000 ppm to about 70000 ppm.

In the fourth aspect, the present disclosure relates to a pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or alternatively from about 5000 ppm to about 70000 ppm.

In the fifth aspect, the present disclosure relates to a process of preparing the lyophilized pharmaceutical composition of phenobarbital or salts thereof having an alcohol content in the range from about 5000 ppm to about 66000 ppm or about 70000 ppm, wherein the process comprises dissolving phenobarbital or salts thereof in water to obtain an aqueous solution of phenobarbital or salts thereof in a concentration of 10-200 mg/ml and lyophilizing the aqueous solution to obtain lyophilized pharmaceutical composition of phenobarbital or salts thereof.

In the sixth aspect, the present disclosure relates to a process of preparing the pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or about 70000 ppm, the process comprises dissolving phenobarbital or salts thereof in water to obtain an aqueous solution having a concentration 10-200 mg/ml; lyophilizing the aqueous solution to obtain lyophilized pharmaceutical composition of phenobarbital or salts thereof; and reconstituting the lyophilized pharmaceutical composition to obtain the pharmaceutical composition of phenobarbital or salts thereof.

In the seventh aspect, the present disclosure relates to a lyophilized pharmaceutical composition of phenobarbital or salts thereof having an alcohol content in the range from about 5000 ppm to about 66000 ppm or alternatively from about 5000 ppm to about 70000 ppm, wherein the lyophilized pharmaceutical composition is obtained by a process comprising: dissolving phenobarbital or salts thereof in water to obtain an aqueous solution having a concentration 10-200 mg/ml and lyophilizing the aqueous solution to obtain lyophilized pharmaceutical composition of phenobarbital or salts thereof.

In the eighth aspect, the present disclosure relates to a pharmaceutical composition of phenobarbital or salts thereof that has been reconstituted from a lyophilized pharmaceutical composition of phenobarbital or salts thereof having an alcohol content in the range from about 5000 ppm to about 66000 ppm or alternatively from about 5000 ppm to about 70000 ppm, wherein the pharmaceutical composition is obtained by a process comprising: dissolving phenobarbital or salts thereof in water to obtain an aqueous solution having a concentration 10-200 mg/ml; lyophilizing the aqueous solution to obtain lyophilized pharmaceutical composition of phenobarbital or salts thereof; and reconstituting the lyophilized pharmaceutical composition to obtain the pharmaceutical composition of phenobarbital or salts thereof.

In the ninth aspect, the present disclosure relates to a lyophilized pharmaceutical composition comprising phenobarbital sodium and ethanol, wherein ethanol is present in an amount sufficient to inhibit degradation of phenobarbital sodium, such that the amount of total impurities present following 36 months of storage at 20-25° C. does not exceed 0.2%.

In the tenth aspect, the present disclosure relates to an aqueous solution for injection comprising phenobarbital sodium and ethanol, wherein ethanol is present in an amount sufficient to inhibit degradation of phenobarbital sodium, such that the amount of total impurities present following 12 hours of storage at 20-25° C. or following 36 hours of storage at 2-8° C. does not exceed 0.2%.

In the eleventh aspect, the present disclosure relates to a process for the preparation of the pharmaceutical composition of phenobarbital or salts thereof, wherein the process comprises dissolving phenobarbital or salt thereof in water to obtain an aqueous solution having a concentration 10-200 mg/ml and lyophilizing the aqueous solution to obtain lyophilized pharmaceutical composition, wherein phenobarbital or salts thereof has an alcohol content in the range from about 5000 ppm to about 66000 ppm or alternatively from about 5000 ppm to about 70000 ppm.

In another aspect, the present disclosure relates to a lyophilized pharmaceutical composition of phenobarbital sodium, wherein the composition has an ethanol content in the range from about 12000 ppm to about 25000 ppm; wherein the composition is stable up to 36 months of storage at 20-25° C. such that the amount of total impurities present following 36 months of storage at 20-25° C. does not exceed 0.2%; and wherein the composition is free of benzyl alcohol and propylene glycol.

In another aspect, the present disclosure relates to an aqueous solution for injection of phenobarbital sodium, wherein the aqueous solution has an ethanol content in the range from about 12000 ppm to about 25000 ppm; wherein the aqueous solution is stable up to 12 hours of storage at 20-25° C. or 36 hours of storage at 2-8° C. such that the amount of total impurities present following 12 hours of storage at 20-25° C. or following 36 hours of storage at 2-8° C. does not exceed 0.2%; wherein the aqueous solution is reconstituted from the lyophilized pharmaceutical composition of phenobarbital sodium; and wherein the aqueous solution is free of benzyl alcohol and propylene glycol.

In another aspect, the present disclosure relates to a lyophilized pharmaceutical composition of phenobarbital or salts thereof, wherein the amount of alcohol in the lyophilized pharmaceutical composition following 36 months of storage at 20-25° C., is in the range from about 5000 ppm to about 66000 ppm or alternatively from about 5000 ppm to about 70000 ppm.

In another aspect, the present disclosure relates to a pharmaceutical composition of phenobarbital or salts thereof that has been reconstituted from a lyophilized pharmaceutical composition of phenobarbital or salts thereof, wherein the amount of alcohol in the pharmaceutical composition following 12 hours of storage at 20-25° C. or 36 hours of storage at 2-8° C., is in the range from about 5000 ppm to 66000 ppm or alternatively from about 5000 ppm to about 70000 ppm.

In another aspect, the present disclosure relates to a method of preventing degradation of phenobarbital or salts thereof, wherein the method comprises dissolving phenobarbital or salts thereof in water to obtain an aqueous solution having a concentration 10-200 mg/ml; and lyophilizing the aqueous solution to obtain lyophilized pharmaceutical composition of phenobarbital or salts thereof, wherein phenobarbital or salts thereof has an alcohol content in the range from about 5000 ppm to about 66000 ppm or alternatively from about 5000 ppm to about 70000 ppm.

DETAILED DESCRIPTION OF THE INVENTION

Definitions

The "phenobarbital or salts thereof" that may be used according to the present disclosure may be phenobarbital base or a phenobarbital salt. The particular salt form of phenobarbital is not particularly limited, and in non-limiting examples, may be, for example, phenobarbital sodium, phenobarbital potassium, phenobarbital benzathine, phenobarbital betaine, or phenobarbital choline. Preferred embodiments utilize a phenobarbital sodium salt.

The term "reconstitution" as used herein, includes the addition of vehicle/diluent in to the lyophilized phenobarbital lyophilized phenobarbital. In preferred embodiments, the vehicle/diluent is water for injection, an aqueous saline solution or an aqueous dextrose solution. In additional preferred embodiments, the vehicle/diluent is water for injection or a 0.9% aqueous saline solution.

The terms "about" as used herein refers to as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value. The term "about" when used in the present application preceding a number and referring to it, is meant to designate any value which lies within the range of ±10%.

The term "total impurities" as used herein, includes known and unknown impurities, either present from the active pharmaceutical ingredient (API) or generated by the degradation of phenobarbital or salts thereof during the manufacturing or stability of the pharmaceutical compositions of the present disclosures. These total impurities includes but not limited to 2-phenyl-2-ethyl acetyl urea, 2-phenyl-2-ethyl-malonamide, α-phenylbutyrylguanidine, 2-phenylbutyric acid and 5-methyl-5-phenylbarbituric acid, and can be represented by following structural formulas:

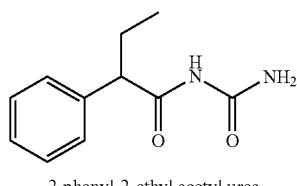

2-phenyl-2-ethyl acetyl urea

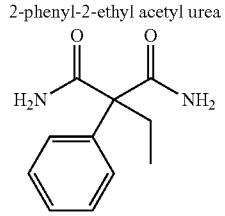

2-phenyl-2-ethyl-malonamide

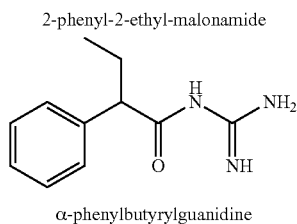

α-phenylbutyrylguanidine

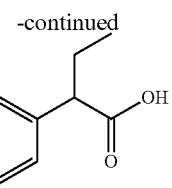

2-phenylbutyric acid

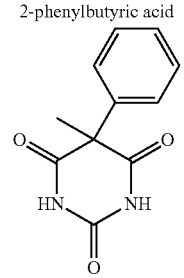

5-methyl-5-phenylbarbituric acid

The term "correctable abnormalities" as used herein is defined as any abnormality which can be corrected by medication. The correctable abnormalities include hypoglycemia or hypocalcemia.

The term "$C_1$-$C_3$ alcohol" as used herein means an alkanol having 1-3 carbon atoms which include methanol, ethanol, 1-propanol, or isopropyl alcohol.

In the first aspect, the present disclosure relates to a pharmaceutical composition of phenobarbital or salts thereof that has been reconstituted from a lyophilized pharmaceutical composition of phenobarbital or salts thereof.

In one embodiment, the pharmaceutical composition of phenobarbital or salts thereof is an aqueous solution for injection.

In one embodiment, the amount of total impurities in the pharmaceutical composition does not exceed 0.2% following 12 hours of storage at 20-25° C. or 36 hours of storage at 2-8° C.

In one embodiment, the present disclosure relates to a pharmaceutical composition of phenobarbital or salts thereof that has been reconstituted from a lyophilized pharmaceutical composition of phenobarbital or salts thereof, wherein the amount of total impurities in the pharmaceutical composition does not exceed 0.2% following 12 hours of storage at 20-25° C. or 36 hours of storage at 2-8° C.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the lyophilized pharmaceutical composition of phenobarbital or salts thereof is reconstituted with water for injection, an aqueous saline or an aqueous dextrose solution. In one embodiment, the lyophilized pharmaceutical composition of phenobarbital or salts thereof is reconstituted with 0.9% of aqueous saline.

In one embodiment, phenobarbital or salts thereof is present in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, phenobarbital or salts thereof is phenobarbital base or phenobarbital sodium, preferably phenobarbital sodium.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment the osmolality of said pharmaceutical composition is below 500 mOsm/kg. In one embodiment, the osmolality of said pharmaceutical composition is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In another aspect, the present disclosure relates to a method for the treatment of neonatal seizure in newborn infants in need thereof, comprising administering the pharmaceutical composition of phenobarbital or salts thereof that has been reconstituted from a lyophilized pharmaceutical composition of phenobarbital or salts thereof, wherein the amount of total impurities in the pharmaceutical composition does not exceed 0.2% following 12 hours of storage at 20-25° C. or 36 hours of storage at 2-8° C.

In one embodiment, the newborn infants is of 2 weeks of age or younger.

In one embodiment, the present disclosure relates to a method for the treatment of neonatal seizure in newborn infants of 2 weeks of age or younger in need thereof, comprising administering the pharmaceutical composition of phenobarbital or salts thereof that has been reconstituted from a lyophilized phenobarbital or salts thereof, wherein the amount of total impurities in the pharmaceutical composition does not exceed 0.2% following 12 hours of storage at 20-25° C. or 36 hours of storage at 2-8° C.

In one embodiment, the method comprises administering the pharmaceutical composition to neonates in whom correctable abnormalities have been excluded or corrected. In one embodiment, the said correctable abnormalities are hypoglycemia or hypocalcemia.

In one embodiment, wherein the pharmaceutical composition is administered intravenously by infusion at a dose of 20 mg/kg over a course of 15 minutes. In one embodiment, the method comprises administration of the pharmaceutical composition at an initial loading dose of 20 mg/kg over a course of 15 minutes and measuring the electrographic seizures, wherein if the electrographic seizures persist or recur after completion of the initial loading dose, a second dose 20 mg/kg is administered over the subsequent 15 minutes for a total loading dose of 40 mg/kg.

Electrographic seizures can be measured by any means and instruments known in the art like electroencephalogram (EEG) or using 2-channel EEG with amplitude-integrated EEG.

In one embodiment, wherein the method for the treatment of neonatal seizure in newborn infants comprising administering the pharmaceutical composition of the first aspect.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the pharmaceutical composition of phenobarbital or salts thereof is an aqueous solution for injection.

In one embodiment, the lyophilized pharmaceutical composition of phenobarbital or salts thereof is reconstituted with water for injection, an aqueous saline or an aqueous dextrose solution. In one embodiment, the lyophilized pharmaceutical composition of phenobarbital or salts thereof is reconstituted with 0.9% of aqueous saline.

In one embodiment, phenobarbital or salts thereof is present in a concentration of 10-200 mg/ml.

In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, phenobarbital or salts thereof is phenobarbital base or phenobarbital sodium, preferably phenobarbital sodium.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment the osmolality of said pharmaceutical composition is below 500 mOsm/kg. In one embodiment, the osmolality of said pharmaceutical composition is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In the second aspect, the present disclosure relates to a pharmaceutical composition of phenobarbital or salts thereof, wherein the pharmaceutical composition has an alcohol content in the range from about 5000 ppm to 66000 ppm or alternatively from about 5000 ppm to about 70000 ppm.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In another embodiment of the second aspect, the pharmaceutical composition is a lyophilized pharmaceutical composition of phenobarbital or salts thereof.

In one embodiment, the lyophilized pharmaceutical composition is stable up to 36 months of storage at 20-25° C.

In one embodiment, the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In another embodiment of the second aspect, the pharmaceutical composition is an aqueous solution for injection of phenobarbital or salts thereof.

In one embodiment, the aqueous solution is reconstituted from the lyophilized pharmaceutical composition of phenobarbital or salts thereof. In one embodiment, the lyophilized pharmaceutical composition is reconstituted with water for injection, an aqueous saline or an aqueous dextrose solution.

In another embodiment, the lyophilized pharmaceutical composition is reconstituted with 0.9% of aqueous saline.

In one embodiment, the aqueous solution comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the aqueous solution is stable up to 12 hours of storage at 20-25° C.

In one embodiment, the amount of total impurities present in the aqueous solution following 12 hours of storage at 20-25° C. does not exceed 0.5%. In one embodiment, the amount of total impurities present in the aqueous solution following 12 hours of storage at 20-25° C. does not exceed 0.2%.

In one embodiment, the aqueous solution is stable up to 36 hours of storage at 2-8° C.

In one embodiment, the amount of total impurities present in the aqueous solution following 36 hours of storage at 2-8° C. does not exceed 0.5%. In one embodiment, the amount of total impurities present in the aqueous solution following 36 hours of storage at 2-8° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the osmolality of said composition is below 500 mOsm/kg. In one embodiment, the osmolality of said aqueous solution is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In another aspect, the present disclosure relates to a method for the treatment of neonatal seizure in newborn infants in need thereof, comprising administering the pharmaceutical composition of phenobarbital or salts thereof, wherein the pharmaceutical composition has an alcohol content in the range from about 5000 ppm to about 66000 ppm or alternatively from about 5000 ppm to about 70000 ppm.

In one embodiment, the newborn infants is 2 weeks of age or younger.

In one embodiment, the present disclosure relates to a method for the treatment of neonatal seizure in newborn infants of 2 weeks of age or younger in need thereof, comprising administering the pharmaceutical composition of phenobarbital or salts thereof, wherein the pharmaceutical composition has an alcohol content in the range from about 5000 ppm to about 66000 ppm or alternatively from about 5000 ppm to about 70000 ppm.

In one embodiment, the method comprises administering the pharmaceutical composition to neonates in whom correctable abnormalities have been excluded or corrected. In one embodiment, the said correctable abnormalities are hypoglycemia or hypocalcemia.

In one embodiment, wherein the pharmaceutical composition of the second aspect is administered intravenously by infusion at a dose of 20 mg/kg over a course of 15 minutes.

In one embodiment, wherein the method comprises administration of the pharmaceutical composition at an initial loading dose of 20 mg/kg over a course of 15 minutes and measuring the electrographic seizures, wherein if the electrographic seizures persist or recur after completion of the initial loading dose, a second dose 20 mg/kg is administered over the subsequent 15 minutes for a total loading dose of 40 mg/kg.

In one embodiment, wherein the method for the treatment of neonatal seizure in newborn infants comprising administering the pharmaceutical composition of the second aspect.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In another embodiment, the pharmaceutical composition is a lyophilized pharmaceutical composition of phenobarbital or salts thereof.

In one embodiment, the lyophilized pharmaceutical composition is stable up to 36 months of storage at 20-25° C.

In one embodiment, the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In another embodiment, the pharmaceutical composition is an aqueous solution for injection of phenobarbital or salts thereof.

In one embodiment, the aqueous solution is reconstituted from the lyophilized pharmaceutical composition of phenobarbital or salts thereof. In one embodiment, the lyophilized pharmaceutical composition is reconstituted with water for injection, an aqueous saline or an aqueous dextrose solution. In another embodiment, the lyophilized pharmaceutical composition is reconstituted with 0.9% of aqueous saline.

In one embodiment, the aqueous solution comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the aqueous solution is stable up to 12 hours of storage at 20-25° C.

In one embodiment, the amount of total impurities present in the aqueous solution following 12 hours of storage at 20-25° C. does not exceed 0.5%. In one embodiment, the amount of total impurities present in the aqueous solution following 12 hours of storage at 20-25° C. does not exceed 0.2%.

In one embodiment, the aqueous solution is stable up to 36 hours of storage at 2-8° C.

In one embodiment, the amount of total impurities present in the aqueous solution following 36 hours of storage at 2-8° C. does not exceed 0.5%. In one embodiment, the amount of total impurities present in the aqueous solution following 36 hours of storage at 2-8° C. does not exceed 0.2%.

In one embodiment, the osmolality of said composition is below 500 mOsm/kg. In one embodiment, the osmolality of said aqueous solution is about 300-400 mOsm/kg.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In the third aspect, the present disclosure relates to a lyophilized pharmaceutical composition of phenobarbital or salts thereof, wherein the composition has an alcohol content in the range from about 5000 ppm to about 66000 ppm or alternatively from about 5000 ppm to about 70000 ppm.

In one embodiment, the lyophilized pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is stable up to 36 months of storage at 20-25° C.

In one embodiment, the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the lyophilized pharmaceutical composition is free of benzyl alcohol.

In one embodiment, the lyophilized pharmaceutical composition is also free of propylene glycol.

In a preferred embodiment, the lyophilized pharmaceutical composition is free of benzyl alcohol and propylene glycol.

In another aspect, the present disclosure relates to a method for the treatment of neonatal seizure in newborn infants in need thereof, comprising administering the lyophilized pharmaceutical composition of phenobarbital or salts thereof, and wherein the lyophilized pharmaceutical composition has an alcohol content in the range from about 5000 ppm to about 66000 ppm.

In one embodiment, the newborn infants is of 2 weeks of age or younger.

In one embodiment, the present disclosure relates to a method for the treatment of neonatal seizure in newborn infants of 2 weeks of age or younger in need thereof, comprising administering the lyophilized pharmaceutical composition of phenobarbital or salts thereof, and wherein the lyophilized pharmaceutical composition has an alcohol content in the range from about 5000 ppm to about 66000 ppm.

In one embodiment, the method comprises reconstituting the lyophilized pharmaceutical composition of phenobarbital or salts thereof immediately prior to the administration.

In one embodiment, the lyophilized pharmaceutical composition is reconstituted with water for injection, an aqueous saline or an aqueous dextrose solution to obtain the aqueous solution for injection of phenobarbital or salts thereof.

In one embodiment, the method comprises administering the aqueous solution to neonates in whom correctable abnormalities have been excluded or corrected. In one embodiment, the said correctable abnormalities are hypoglycemia or hypocalcemia.

In one embodiment, wherein the aqueous solution is administered intravenously by infusion at a dose of 20 mg/kg over a course of 15 minutes.

In one embodiment, wherein the method comprises administration of the aqueous solution at an initial loading dose of 20 mg/kg over a course of 15 minutes and measuring the electrographic seizures, wherein if the electrographic seizures persist or recur after completion of the initial loading dose, a second dose 20 mg/kg is administered over the subsequent 15 minutes for a total loading dose of 40 mg/kg.

In one embodiment, wherein the method for the treatment of neonatal seizure in newborn infants comprising administering the lyophilized pharmaceutical composition of the third aspect.

In one embodiment, the lyophilized pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is stable up to 36 months of storage at 20-25° C.

In one embodiment, the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the lyophilized pharmaceutical composition is free of benzyl alcohol.

In one embodiment, the lyophilized pharmaceutical composition is also free of propylene glycol.

In a preferred embodiment, the lyophilized pharmaceutical composition is free of benzyl alcohol and propylene glycol.

In the fourth aspect, the present disclosure relates to a pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or alternatively from about 5000 ppm to about 70000 ppm.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is reconstituted with water for injection, an aqueous saline or an aqueous dextrose solution. In one embodiment, the lyophilized pharmaceutical composition is reconstituted with 0.9% aqueous saline.

In one embodiment, the pharmaceutical composition is an aqueous solution for injection of phenobarbital or salts thereof.

In one embodiment, the pharmaceutical composition comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the pharmaceutical composition is stable up to 12 hours of storage at 20-25° C.

In one embodiment, the amount of total impurities present in the pharmaceutical composition following 12 hours of storage at 20-25° C. does not exceed 0.5%. In one embodiment, the amount of total impurities present in the pharmaceutical composition following 12 hours of storage at 20-25° C. does not exceed 0.2%.

In one embodiment, the pharmaceutical composition is stable up to 36 hours of storage at 2-8° C.

In one embodiment, the amount of total impurities present in the pharmaceutical composition following 36 hours of storage at 2-8° C. does not exceed 0.5%. In one embodiment, the amount of total impurities present in the pharmaceutical composition following 36 hours of storage at 2-8° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the osmolality of said pharmaceutical composition is below 500 mOsm/kg. In one embodiment, the osmolality of said aqueous solution is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In another aspect, the present disclosure relates to a method for the treatment of neonatal seizure in newborn infants in need thereof, comprising administering the pharmaceutical composition of phenobarbital or salts thereof that has been reconstituted from a lyophilized pharmaceutical composition of phenobarbital or salts thereof, and wherein the pharmaceutical composition has an alcohol content in the range from about 5000 ppm to about 66000 ppm or alternatively from about 5000 ppm to about 70000 ppm.

In one embodiment, the newborn infants is of 2 weeks of age or younger.

In one embodiment, the present disclosure relates to a method for the treatment of neonatal seizure in newborn infants of 2 weeks of age or younger in need thereof, comprising administering the pharmaceutical composition of phenobarbital or salts thereof that has been reconstituted from a lyophilized pharmaceutical composition of phenobarbital or salts thereof, and wherein the pharmaceutical composition has an alcohol content in the range from about 5000 ppm to about 66000 ppm or alternatively from about 5000 ppm to about 70000 ppm.

In one embodiment, the method comprises administering the pharmaceutical composition to neonates in whom correctable abnormalities have been excluded or corrected. In one embodiment, the said correctable abnormalities are hypoglycemia or hypocalcemia.

In one embodiment, wherein the pharmaceutical composition is administered intravenously by infusion at a dose of 20 mg/kg over a course of 15 minutes.

In one embodiment, wherein the method comprises administration of the pharmaceutical composition at an initial loading dose of 20 mg/kg over a course of 15 minutes and measuring the electrographic seizures, wherein if the electrographic seizures persist or recur after completion of the initial loading dose, a second dose 20 mg/kg is administered over the subsequent 15 minutes for a total loading dose of 40 mg/kg.

In one embodiment, wherein the method for the treatment of neonatal seizure in newborn infants comprising administering the pharmaceutical composition of the fourth aspect.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is reconstituted with water for injection, an aqueous saline or an aqueous dextrose solution. In one embodiment, the lyophilized pharmaceutical composition is reconstituted with 0.9% aqueous saline.

In one embodiment, the pharmaceutical composition is an aqueous solution for injection of phenobarbital or salts thereof.

In one embodiment, the pharmaceutical composition comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the pharmaceutical composition is stable up to 12 hours of storage at 20-25° C.

In one embodiment, the amount of total impurities present in the pharmaceutical composition following 12 hours of storage at 20-25° C. does not exceed 0.5%. In one embodiment, the amount of total impurities present in the pharmaceutical composition following 12 hours of storage at 20-25° C. does not exceed 0.2%.

In one embodiment, the pharmaceutical composition is stable up to 36 hours of storage at 2-8° C.

In one embodiment, the amount of total impurities present in the pharmaceutical composition following 36 hours of storage at 2-8° C. does not exceed 0.5%. In one embodiment, the amount of total impurities present in the pharmaceutical composition following 36 hours of storage at 2-8° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the osmolality of the pharmaceutical composition is below 500 mOsm/kg. In one embodiment, the osmolality of the pharmaceutical composition is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In the fifth aspect, the present disclosure relates to a process of preparing the lyophilized pharmaceutical composition of phenobarbital or salts thereof having an alcohol content in the range from about 5000 ppm to about 66000 ppm or alternatively from about 5000 ppm to about 70000 ppm, wherein the process comprises dissolving phenobarbital or salts thereof in water to obtain an aqueous solution of phenobarbital or salts thereof in a concentration of 10-200 mg/ml and lyophilizing the aqueous solution to obtain lyophilized pharmaceutical composition of phenobarbital or salts thereof.

In one embodiment, the process comprises measuring the alcohol content of an aqueous solution of phenobarbital or salts thereof. In one embodiment, if the alcohol content of the aqueous solution is below 5000 ppm then the process further comprises a step of adding an alcohol in a quantity that is sufficient to achieve the alcohol content of at least about 5000 ppm.

In one embodiment, the process comprises measuring the alcohol content of the lyophilized pharmaceutical composition of phenobarbital or salts thereof. In one embodiment, the process may comprises repeating steps of lyophilization to achieve the alcohol content not more than about 66000 ppm or about 70000 ppm. In one embodiment, if the alcohol content is above 66000 ppm or 70000 ppm (whichever is desired), the process further comprises repeating the lyophilization step till the alcohol content of the lyophilized pharmaceutical composition is not more than about 66000 ppm or not more than about 70000 ppm. It is understood that even a single additional cycle of lyophilization would be sufficient or it has to be repeated n number of times to obtain the desired alcohol level.

In another aspect, the present disclosure relates to a process of preparing the lyophilized pharmaceutical composition of phenobarbital or salts thereof having an alcohol content in the range from about 5000 ppm to about 66000 ppm or alternatively from about 5000 ppm to about 70000 ppm, wherein the process comprises dissolving phenobarbital or salts thereof in water to obtain an aqueous solution having a concentration 10-200 mg/ml; measuring the alcohol content of aqueous solution; if the alcohol content is below 5000 ppm, adding an alcohol to achieve the alcohol content of at least about 5000 ppm; lyophilizing the aqueous solution to obtain lyophilized pharmaceutical composition; measuring the alcohol content of the lyophilized pharmaceutical composition; if the alcohol content is above 66000 ppm or above about 70000 ppm (whichever is desired), repeating the lyophilization step multiple times till the alcohol content of the lyophilized pharmaceutical composition is not more than about 66000 ppm or is not more than about 70000 ppm.

In one embodiment, the process comprises addition of a pH modifier to the aqueous solution of phenobarbital or salts thereof to achieve a pH in a range of 8-12, preferably in a range of 9-11, more preferably in a range of 9-10.5.

In one embodiment, the pH modifier is selected from HCl and/or NaOH. In one embodiment, the pH modifier is aqueous HCl solution.

In one embodiment, the lyophilized pharmaceutical composition is stable up to 36 months of storage at 20-25° C.

In one embodiment, the lyophilized pharmaceutical composition has an alcohol content of at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is stable up to 36 months of storage at 20-25° C.

In one embodiment, the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the lyophilized pharmaceutical composition is free of benzyl alcohol.

In one embodiment, the lyophilized pharmaceutical composition is also free of propylene glycol.

In a preferred embodiment, the lyophilized pharmaceutical composition is free of benzyl alcohol and propylene glycol.

In the sixth aspect, the present disclosure relates to a process of preparing the pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or alternatively from about 5000 ppm to about 70000 ppm, wherein the process comprises dissolving phenobarbital or salts thereof in water to obtain an aqueous solution having a concentration 10-200 mg/ml; lyophilizing the aqueous solution to obtain lyophilized pharmaceutical composition of phenobarbital or salts thereof; and reconstituting the lyophilized pharmaceutical composition to obtain the pharmaceutical composition of phenobarbital or salts thereof.

In one embodiment, the process comprises measuring the alcohol content of an aqueous solution of phenobarbital or salts thereof. In one embodiment, if the alcohol content of the aqueous solution is below 5000 ppm then the process further comprises a step of adding an alcohol in a quantity that is sufficient to achieve the alcohol content of at least about 5000 ppm.

In one embodiment, the process comprises measuring the alcohol content of the lyophilized pharmaceutical composition of phenobarbital or salts thereof. In one embodiment, the process may comprises additional steps of lyophilization to achieve the alcohol content not more than about 66000 ppm or not more than about 70000 ppm (whichever is desired). In one embodiment, if the alcohol content is above 66000 ppm or about 70000 ppm, the process further comprises repeating the lyophilization step till the alcohol content of the lyophilized pharmaceutical composition is not more than about 66000 ppm or not more than about 70000 ppm. It is understood that even a single additional cycle of lyophilization would be sufficient or it has to be repeated n number of times to obtain the desired alcohol level.

In another aspect, the present disclosure relates to a process of preparing the pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or alternatively from about 5000 ppm to about 70000 ppm, wherein the process comprises dissolving phenobarbital or salts thereof in water to obtain an aqueous solution having a concentration 10-200 mg/ml; measuring the alcohol content of aqueous solution; if the alcohol content is below 5000 ppm, adding an alcohol to achieve the alcohol content of at least about 5000 ppm; lyophilizing the aqueous solution to obtain lyophilized pharmaceutical composition; measuring the alcohol content of the lyophilized pharmaceutical composition; if the alcohol content is above 66000 ppm or about 70000 ppm (whichever is desired), repeating the lyophilization step multiple times till the alcohol content of the lyophilized pharmaceutical composition is not more than about 66000 ppm or not more than about 70000 ppm (whichever is desired); and reconstituting the lyophilized pharmaceutical composition to obtain the pharmaceutical composition of phenobarbital or salts thereof.

In one embodiment, the process comprises addition of a pH modifier to the aqueous solution of phenobarbital or salts thereof to achieve a pH in a range of 8-12, preferably in a range of 9-11, more preferably in a range of 9-10.5. In one embodiment, the pH modifier is selected from HCl and/or NaOH. In one embodiment, the pH modifier is aqueous HCl solution.

In one embodiment, the lyophilized pharmaceutical composition is reconstituted with water for injection, an aqueous saline or an aqueous dextrose solution. In one embodiment, the lyophilized pharmaceutical composition is reconstituted with 0.9% aqueous saline.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the pharmaceutical composition is an aqueous solution for injection of phenobarbital or salts thereof.

In one embodiment, the pharmaceutical composition comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the pharmaceutical composition is stable up to 12 hours of storage at 20-25° C.

In one embodiment, the amount of total impurities in the pharmaceutical composition present following 12 hours of storage at 20-25° C. does not exceed 0.5%. In one embodiment, the amount of total impurities present in the pharmaceutical composition following 12 hours of storage at 20-25° C. does not exceed 0.2%.

In one embodiment, the pharmaceutical composition is stable up to 36 hours of storage at 2-8° C.

In one embodiment, the amount of total impurities present in the pharmaceutical composition following 36 hours of storage at 2-8° C. does not exceed 0.5%. In one embodiment, the amount of total impurities present in the pharmaceutical composition following 36 hours of storage at 2-8° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the osmolality of the pharmaceutical composition is below 500 mOsm/kg. In one embodiment, the osmolality of the pharmaceutical composition is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In the seventh aspect, the present disclosure relates to a lyophilized pharmaceutical composition of phenobarbital or salts thereof having an alcohol content in the range from about 5000 ppm to about 66000 ppm or alternatively from about 5000 ppm to about 70000 ppm, wherein the lyophilized pharmaceutical composition is obtained by a process comprising: dissolving phenobarbital or salts thereof in water to obtain an aqueous solution having a concentration 10-200 mg/ml and lyophilizing the aqueous solution to obtain lyophilized pharmaceutical composition of phenobarbital or salts thereof.

In one embodiment, the process comprises measuring the alcohol content of an aqueous solution of phenobarbital or salts thereof. In one embodiment, if the alcohol content of the aqueous solution is below 5000 ppm then the process further comprises a step of adding an alcohol in a quantity that is sufficient to achieve the alcohol content of at least about 5000 ppm.

In one embodiment, the process comprises measuring the alcohol content of the lyophilized pharmaceutical composition of phenobarbital or salts thereof. In one embodiment, the process may comprises an additional step of lyophilization to achieve the alcohol content not more than about 66000 ppm or not more than 70000 ppm (whichever is desired). In one embodiment, if the alcohol content is above 66000 ppm or about 70000 ppm, the process further comprises repeating the lyophilization step till the alcohol content of the lyophilized pharmaceutical composition is not more than about 66000 ppm or not more than about 70000 ppm (whichever is desired). It is understood that even a single additional cycle of lyophilization would be sufficient or it has to be repeated n number of times to obtain the desired alcohol level.

In one embodiment, the process comprises addition of a pH modifier to the aqueous solution of phenobarbital or salts thereof to achieve a pH in a range of 8-12, preferably in a range of 9-11, more preferably in a range of 9-10.5.

In one embodiment, the pH modifier is selected from HCl and/or NaOH. In one embodiment, the pH modifier is aqueous HCl solution.

In one embodiment, the lyophilized pharmaceutical composition has an alcohol content of at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is stable up to 36 months of storage at 20-25° C.

In one embodiment, the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the lyophilized pharmaceutical composition is free of benzyl alcohol.

In one embodiment, the lyophilized pharmaceutical composition is also free of propylene glycol.

In a preferred embodiment, the lyophilized pharmaceutical composition is free of benzyl alcohol and propylene glycol.

In order to achieve a desired stability, the lyophilized pharmaceutical composition should have an alcohol content in the range from about 5000 ppm to 66000 ppm or alternatively from about 5000 ppm to about 70000 ppm, and thus the process may include the steps as discussed above for measuring the alcohol content, adding alcohol or removing additional alcohol by repeating the lyophilization step and ensuring that the alcohol content is achieved as described above.

In the eight aspect, the present disclosure relates to a pharmaceutical composition of phenobarbital or salts thereof that has been reconstituted from a lyophilized pharmaceutical composition of phenobarbital or salts thereof having an alcohol content in the range from about 5000 ppm to about 66000 ppm or alternatively from about 5000 ppm to about 70000 ppm, wherein the pharmaceutical composition is obtained by a process comprising: dissolving phenobarbital or salts thereof in water to obtain an aqueous solution having a concentration 10-200 mg/ml; lyophilizing the aqueous solution to obtain lyophilized pharmaceutical composition of phenobarbital or salts thereof; and reconstituting the lyophilized pharmaceutical composition to obtain the pharmaceutical composition of phenobarbital or salts thereof.

In one embodiment, the process comprises measuring the alcohol content of an aqueous solution of phenobarbital or salts thereof. In one embodiment, if the alcohol content of the aqueous solution is below 5000 ppm then the process further comprises a step of adding an alcohol in a quantity that is sufficient to achieve the alcohol content of at least about 5000 ppm.

In one embodiment, the process comprises measuring the alcohol content of the lyophilized pharmaceutical composition of phenobarbital or salts thereof. In one embodiment, the process may comprises an additional step of lyophilization to achieve the alcohol content not more than about 66000 ppm or not more than about 70000 ppm (whichever is desired). In one embodiment, if the alcohol content is above about 66000 ppm or above about 70000 ppm, the process further comprises repeating the lyophilization step till the alcohol content of the lyophilized pharmaceutical composition is not more than about 66000 ppm or not more than about 70000 ppm (whichever is desired). It is understood that even a single additional cycle of lyophilization would be sufficient or it has to be repeated n number of times to obtain the desired alcohol level.

In one embodiment, the process comprises addition of a pH modifier to the aqueous solution of phenobarbital or salts thereof to achieve a pH in a range of 8-12, preferably in a range of 9-11, more preferably in a range of 9-10.5.

In one embodiment, the pH modifier is selected from HCl and/or NaOH. In one embodiment, the pH modifier is aqueous HCl solution.

In one embodiment, the lyophilized pharmaceutical composition is reconstituted with water for injection, an aqueous saline or an aqueous dextrose solution. In one embodiment, the lyophilized pharmaceutical composition is reconstituted with 0.9% aqueous saline.

In one embodiment, the pharmaceutical composition has an alcohol content in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the pharmaceutical composition is an aqueous solution for injection of phenobarbital or salts thereof.

In one embodiment, the pharmaceutical composition comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the pharmaceutical composition is stable up to 12 hours of storage at 20-25° C.

In one embodiment, the amount of total impurities present in the pharmaceutical composition following 12 hours of storage at 20-25° C. does not exceed 0.5%. In one embodiment, the amount of total impurities present in the pharmaceutical composition following 12 hours of storage at 20-25° C. does not exceed 0.2%.

In one embodiment, the pharmaceutical composition is stable up to 36 hours of storage at 2-8° C.

In one embodiment, the amount of total impurities present in the pharmaceutical composition following 36 hours of storage at 2-8° C. does not exceed 0.5%. In one embodiment, the amount of total impurities present in the pharmaceutical composition following 36 hours of storage at 2-8° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the osmolality of the pharmaceutical composition is below 500 mOsm/kg. In one embodiment, the osmolality of the pharmaceutical composition is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In order to achieve a desired stability, the pharmaceutical composition should have an alcohol content in the range from about 5000 ppm to 66000 ppm or alternatively from about 5000 ppm to about 70000 ppm, and thus the process may include the steps as discussed above for measuring the alcohol content, adding alcohol or removing additional alcohol by repeating the lyophilization step and ensuring that the alcohol content is achieved as described above.

In the ninth aspect, the present disclosure relates to a lyophilized pharmaceutical composition comprising phenobarbital or salts thereof and an alcohol.

In one embodiment, the alcohol is present in an amount sufficient to inhibit phenobarbital degradation, such that the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the amount of alcohol sufficient to inhibit phenobarbital degradation is in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is stable up to 36 months of storage at 20-25° C.

In one embodiment, the lyophilized pharmaceutical composition is free of benzyl alcohol.

In one embodiment, the lyophilized pharmaceutical composition is also free of propylene glycol.

In a preferred embodiment, the lyophilized pharmaceutical composition is free of benzyl alcohol and propylene glycol.

In one embodiment, the present disclosure relates to a lyophilized pharmaceutical composition comprising phenobarbital sodium and ethanol, wherein ethanol is present in an amount sufficient to inhibit degradation of phenobarbital sodium, such that the amount of total impurities present in the lyophilized pharmaceutical composition following 36 months of storage at 20-25° C. does not exceed 0.2%;
wherein the amount of ethanol sufficient to inhibit degradation of phenobarbital sodium is in the range from about 12000 ppm to about 25000 ppm;
and wherein the pharmaceutical composition is free of benzyl alcohol and propylene glycol.

In the tenth aspect, the present disclosure relates to an aqueous solution for injection comprising phenobarbital or salts thereof and an alcohol.

In one embodiment, the aqueous solution for injection is reconstituted from the lyophilized pharmaceutical composition of phenobarbital or salts thereof.

In one embodiment, the lyophilized pharmaceutical composition is reconstituted with water for injection, an aqueous saline or an aqueous dextrose solution.

In one embodiment, the alcohol is present in an amount sufficient to inhibit phenobarbital degradation, such that the amount of total impurities present in the aqueous solution following 12 hours of storage at 20-25° C. does not exceed 0.5%. In one embodiment, the amount of total impurities present in the aqueous solution following 12 hours of storage at 20-25° C. does not exceed 0.2%.

In one embodiment, the alcohol is present in an amount sufficient to inhibit phenobarbital degradation, such that the amount of total impurities present in the aqueous solution following 36 hours of storage at 2-8° C. does not exceed 0.5%. In one embodiment, the amount of total impurities present in the aqueous solution following 36 hours of storage at 2-8° C. does not exceed 0.2%.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the amount of alcohol sufficient to inhibit phenobarbital degradation is in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the aqueous solution comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the aqueous solution is stable up to 12 hours of storage at 20-25° C.

In one embodiment, the aqueous solution is stable up to 36 hours of storage at 2-8° C.

In one embodiment, the osmolality of the aqueous solution is below 500 mOsm/kg. In one embodiment, the osmolality of the aqueous solution is about 300-400 mOsm/kg.

In one embodiment, the aqueous solution is free of benzyl alcohol.

In one embodiment, the aqueous solution is also free of propylene glycol.

In a preferred embodiment, the aqueous solution is free of benzyl alcohol and propylene glycol.

In one embodiment, the present disclosure relates to an aqueous solution for injection comprising phenobarbital sodium and ethanol, wherein ethanol is present in an amount sufficient to inhibit degradation of phenobarbital sodium, such that the amount of total impurities present in the aqueous solution following 12 hours of storage at 20-25° C. or following 36 hours of storage at 2-8° C. does not exceed 0.2%;

wherein the amount of ethanol sufficient to inhibit degradation of phenobarbital sodium is in the range from about 12000 ppm to about 25000 ppm;

wherein phenobarbital sodium is present in a concentration from 10-200 mg/ml;

wherein the aqueous solution is reconstituted from the lyophilized pharmaceutical composition of phenobarbital sodium;

and wherein the aqueous solution is free of benzyl alcohol and propylene glycol.

In the eleventh aspect, the present disclosure relates to a process for the preparation of the pharmaceutical composition of phenobarbital or salts thereof, wherein the process comprises dissolving phenobarbital or salt thereof in water to obtain an aqueous solution having a concentration 10-200 mg/ml and lyophilizing the aqueous solution to obtain lyophilized pharmaceutical composition, wherein phenobarbital or salts thereof has an alcohol content in the range from about 5000 ppm to about 66000 ppm or alternatively from about 5000 ppm to about 70000 ppm.

In one embodiment, the process comprises phenobarbital or salts thereof having an alcohol content in the range from about 5000 ppm to about 66000 ppm or alternatively from about 5000 ppm to about 70000 ppm. In one embodiment, the active pharmaceutical ingredient of phenobarbital or salts thereof for the purpose of this aspect is having an alcohol content in the range from about 5000 ppm to about 66000 ppm or alternatively from about 5000 ppm to about 70000 ppm.

In one embodiment, the process further comprises reconstitution of the lyophilized pharmaceutical composition. In one embodiment, the lyophilized pharmaceutical composition is reconstituted with water for injection, an aqueous saline or an aqueous dextrose solution. In one embodiment, the lyophilized pharmaceutical composition is reconstituted with 0.9% aqueous saline.

In one embodiment, phenobarbital or salts thereof has an alcohol content of at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In one embodiment, the pharmaceutical composition is lyophilized pharmaceutical composition of phenobarbital or salts thereof.

In one embodiment, the lyophilized pharmaceutical composition is stable up to 36 months of storage at 20-25° C.

In one embodiment, the amount of total impurities present in the lyophilized pharmaceutical composition following 36 months of storage at 20-25° C. does not exceed 0.5%. In one embodiment, the amount of total impurities present in the lyophilized pharmaceutical composition following 36 months of storage at 20-25° C. does not exceed 0.2%.

In one embodiment, the pharmaceutical composition is an aqueous solution for injection of phenobarbital or salts thereof.

In one embodiment, the aqueous solution comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the aqueous solution is stable up to 12 hours of storage at 20-25° C.

In one embodiment, the amount of total impurities present in the aqueous solution following 12 hours of storage at 20-25° C. does not exceed 0.5%. In one embodiment, the amount of total impurities present in the aqueous solution following 12 hours of storage at 20-25° C. does not exceed 0.2%.

In one embodiment, the aqueous solution is stable up to 36 hours of storage at 2-8° C.

In one embodiment, the amount of total impurities present in the aqueous solution following 36 hours of storage at 2-8° C. does not exceed 0.5%. In one embodiment, the amount of total impurities present in the aqueous solution following 36 hours of storage at 2-8° C. does not exceed 0.2%.

In one embodiment, the osmolality of the aqueous solution is below 500 mOsm/kg. In one embodiment, the osmolality of the aqueous solution is about 300-400 mOsm/kg.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In another aspect, the present disclosure relates to a lyophilized pharmaceutical composition of phenobarbital or salts thereof, wherein the lyophilized pharmaceutical composition has: (i) an amount of alcohol present following 36 months of storage at 20-25° C. in the range from about 5000 ppm to about 66000 ppm or alternatively from about 5000 ppm to about 70000 ppm; or (ii) an amount of total impurities present following 36 months of storage at 20-25° C. does not exceed 0.2%.

In one embodiment, the lyophilized pharmaceutical composition has an amount of alcohol present following 36 months of storage at 20-25° C. in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm.

In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is stable up to 36 months of storage at 20-25° C.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the lyophilized pharmaceutical composition is free of benzyl alcohol.

In one embodiment, the lyophilized pharmaceutical composition is also free of propylene glycol.

In a preferred embodiment, the lyophilized pharmaceutical composition is free of benzyl alcohol and propylene glycol.

In another aspect, the present disclosure relates to a pharmaceutical composition of phenobarbital or salts thereof that has been reconstituted from a lyophilized pharmaceutical composition of phenobarbital or salts thereof, wherein the pharmaceutical composition has: (i) an amount of alcohol present following 12 hours of storage at 20-25° C. or 36 hours of storage at 2-8° C. in the range from about 5000 ppm to about 66000 ppm or alternatively from about 5000 ppm to about 70000 ppm; or (ii) an amount of total impurities present following 12 hours of storage at 20-25° C. or 36 hours of storage at 2-8° C. does not exceed 0.2%.

In one embodiment, the pharmaceutical composition has an amount of alcohol present following 12 hours of storage at 20-25° C. or 36 hours of storage at 2-8° C. in the range from about 5000 ppm to about 66000 ppm or alternatively from about 5000 ppm to about 70000 ppm. In one embodiment, the alcohol content is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In one embodiment, the lyophilized pharmaceutical composition is reconstituted with water for injection, an aqueous saline or an aqueous dextrose solution. In one embodiment, the lyophilized pharmaceutical composition is reconstituted with 0.9% aqueous saline.

In one embodiment, the pharmaceutical composition is an aqueous solution for injection of phenobarbital or salts thereof.

In one embodiment, the pharmaceutical composition comprise phenobarbital or salts thereof in a concentration of 10-200 mg/ml. In one embodiment, phenobarbital or salts thereof is present in a concentration of 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml and 200 mg/ml.

In one embodiment, the pharmaceutical composition is stable up to 12 hours of storage at 20-25° C.

In one embodiment, the pharmaceutical composition is stable up to 36 hours of storage at 2-8° C.

In one embodiment, the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

In one embodiment, the osmolality of said pharmaceutical composition is below 500 mOsm/kg. In one embodiment, the osmolality of said aqueous solution is about 300-400 mOsm/kg.

In one embodiment, the pharmaceutical composition is free of benzyl alcohol.

In one embodiment, the pharmaceutical composition is also free of propylene glycol.

In a preferred embodiment, the pharmaceutical composition is free of benzyl alcohol and propylene glycol.

In another aspect, the present disclosure relates to a lyophilized pharmaceutical composition of phenobarbital sodium, wherein the composition has an ethanol content in the range from about 12000 ppm to about 25000 ppm; wherein the composition is stable up to 36 months of storage at 20-25° C. such that the amount of total impurities present following 36 months of storage at 20-25° C. does not exceed 0.2%; and wherein the composition is free of benzyl alcohol and propylene glycol.

In another aspect, the present disclosure relates to an aqueous solution for injection of phenobarbital sodium, wherein the aqueous solution has an ethanol content in the range from about 12000 ppm to about 25000 ppm; wherein the aqueous solution is stable up to 12 hours of storage at 20-25° C. or 36 hours of storage at 2-8° C. such that the amount of total impurities present following 12 hours of storage at 20-25° C. or following 36 hours of storage at 2-8° C. does not exceed 0.2%; wherein the aqueous solution is reconstituted from the lyophilized pharmaceutical composition of phenobarbital sodium; and wherein the aqueous solution is free of benzyl alcohol and propylene glycol.

In another aspect, the present disclosure relates to a method of preventing degradation of phenobarbital or salts thereof, wherein the method comprises dissolving phenobarbital or salts thereof in water to obtain an aqueous solution having a concentration 10-200 mg/ml; and lyophilizing the aqueous solution to obtain lyophilized pharmaceutical composition of phenobarbital or salts thereof, wherein the method comprises presence of alcohol, in an amount sufficient to inhibit the degradation of phenobarbital or salts thereof.

In one embodiment, the present disclosure relates to reconstituting the lyophilized pharmaceutical composition to obtain the aqueous solution for injection of phenobarbital or salts thereof.

In one embodiment, wherein the amount of alcohol sufficient to inhibit degradation of phenobarbital or salts thereof is in the range from about 5000 ppm to about 66000 ppm or alternatively from about 5000 ppm to about 70000 ppm. In one embodiment, the amount of alcohol is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm.

In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

In yet another aspect, the present invention relates to phenobarbital or salts thereof having an alcohol in an amount sufficient to inhibit degradation of phenobarbital sodium.

In one embodiment, the amount of alcohol sufficient to inhibit degradation of phenobarbital or salts thereof is such that when said phenobarbital or salts thereof having an alcohol is stored for 36 months at 20-25° C., the amount of total impurities does not exceed 0.5%, preferably does not exceed 0.2%.

In an alternate embodiment, the amount of alcohol sufficient to inhibit degradation of phenobarbital or salts thereof is such that when said phenobarbital or salts thereof is dissolved in an aqueous media and is stored for 12 hours at 20-25° C. or 36 hours at 2-8° C., the amount of total impurities does not exceed 0.5%, preferably does not exceed 0.2%. In one embodiment, the amount of alcohol sufficient to inhibit degradation of phenobarbital or salts thereof is from about 5000 ppm to about 70000 ppm.

In one embodiment, the phenobarbital or salts thereof having an alcohol content in a range from about 5000 ppm to about 70000 ppm, is stable up to 36 months of storage at 20-25° C. such that the amount of total impurities present following 36 months of storage at 20-25° C. does not exceed 0.5%, preferably does not exceed 0.2%.

In another embodiment, the phenobarbital or salts thereof having an alcohol content in a range from about 5000 ppm to about 70000 ppm, when dissolved in an aqueous media, the resulting aqueous solution of phenobarbital or salts thereof remains stable up to 12 hours of storage at 20-25° C. or 36 hours of storage at 2-8° C. such that the amount of total impurities present following 12 hours of storage at 20-25° C. or following 36 hours of storage at 2-8° C. does not exceed 0.5%, preferably does not exceed 0.2%.

In one embodiment, the amount of alcohol is at least about 5000 ppm, about 10000 ppm, about 15000 ppm, about 20000 ppm, about 25000 ppm, about 30000 ppm, about 35000 ppm, about 40000 ppm, about 45000 ppm, about 50000 ppm, about 55000 ppm, about 60000 ppm, about 65000 ppm, about 66000 ppm, or about 70000 ppm. In another embodiment, the alcohol content is in the range from about 12000 ppm to about 70000 ppm, about 12000 ppm to about 66000 ppm, about 12000 ppm to about 65000 ppm, about 12000 ppm to about 60000 ppm, about 12000 ppm to about 55000 ppm, about 12000 ppm to about 50000 ppm, about 12000 ppm to about 45000 ppm, about 12000 ppm to about 40000 ppm, about 12000 ppm to about 35000 ppm, about 12000 ppm to about 30000 ppm, about 12000 ppm to about 25000 ppm, about 12000 ppm to about 20000 ppm or about 12000 ppm to about 15000 ppm. In another embodiment, the alcohol content is in the range from about 15000 ppm to about 70000 ppm, about 15000 ppm to about 66000 ppm, about 25000 ppm to about 66000 ppm, about 35000 to about 66000 ppm, about 45000 ppm to about 66000 ppm, about 55000 ppm to about 66000 ppm, about 35000 ppm to about 55000 ppm or about 30000 ppm to about 50000 ppm.

In another embodiment, the alcohol content is in the range from about 12000 ppm to about 25000 ppm. In one embodiment, the alcohol content is in the range from about 35000 to about 66000 ppm.

In one embodiment, the alcohol is a $C_1$-$C_3$ alcohol.

In one embodiment, the alcohol is ethanol.

In one embodiment, phenobarbital or salts thereof is phenobarbital base or phenobarbital sodium, preferably phenobarbital sodium.

Through lyophilization, the present inventors have found that the alcohol content of phenobarbital sodium may be reduced to less than 50000 ppm. The present inventors have found that in some embodiments, the alcohol content may be reduced to a level of about 5000 ppm. The present inventors have found that the low temperature vacuum drying conditions afforded by lyophilization provide a safe and effective mechanism for converting the tested material to a solid state. Lyophilization, also known as freeze drying, may consist of three separate, unique, and interdependent process; freezing, primary drying (sublimation) and secondary drying (desorption).

In certain preferred embodiments, the step of freezing the aqueous solution may occur at a temperature range of −20 to −50° C. In certain preferred embodiments, the step drying the aqueous solution may occur at primary and/or secondary temperature ranges of −35 to 25° C. However, it should be understood that these temperatures are exemplary only, and temperatures may be chosen so as to optimize the lyophilized powder. Where secondary temperature ranges are used, the step of drying may be split into two separate steps, each occurring at a different temperature and a different time. In certain preferred embodiments, there may also be performed a step of annealing the aqueous solution, which may occur at a temperature range of −15 to −25°. In certain embodiments, a desired level of residual water content after lyophilization may be less than 3% w/w.

As illustrated in the Examples below, the present inventors have observed that the use of certain level of alcohol and lyophilization in the development of the pharmaceutical composition of phenobarbital or slats thereof provides for greatly improved stability in the resulting product.

EXAMPLES

HPLC Method:
HPLC instrument with UV detector or PDA detector;
Reagents/Solvents: Potassium dihydrogen phosphate, Orthophosphoric acid, Acetonitrile, Methanol, Water, Water for Injection;
Needle wash solutions—Water:Methanol (20:80 v/v) & Column wash solution—Water Acetonitrile (50:50 v/v);
Preparation of diluted orthophosphoric acid: Dilute 1 ml of concentrated orthophosphoric acid to 10 ml with water;
Preparation of Buffer: Weigh about 2.9 g (2.85 g to 2.95 g) of potassium dihydrogen phosphate and dissolve in 1000 ml of Milli-Q water, adjust pH to 3.5±0.05 with dilute orthophosphoric acid.
Filter the solution through 0.45 PVDF Merck Durapore membrane or equivalent filter.
Preparation of Mobile Phase Solutions: Mobile Phase A: Buffer to Acetonitrile (80:20) & Mobile Phase B: Buffer to Acetonitrile (50:50); Diluent: water:methanol (20:80)
Chromatographic Conditions:
Column Zorbax Eclipse XDB Phenyl, 150×4.6 mm, 5 m (Agilent)
Column temperature 40° C.
Sample Cooler 10° C.
Flow rate 1.2 ml/min
Injection Volume 10 μl Wavelength 210 nm (UV/PDA)
Run Time 15 minutes
HPLC Gradient:

| Time (minute) | Mobile phase A % | Mobile phase B % |
| --- | --- | --- |
| 0 | 80 | 20 |
| 4 | 80 | 20 |
| 7 | 20 | 80 |
| 12 | 20 | 80 |
| 12.1 | 80 | 20 |
| 15 | 80 | 20 |

Example 1

In a clean and dry flask, 1000 mg of phenobarbital base and 1.67 ml of 96% ethanol were combined and mixed for 1 minute. To this solution, 1.722 ml of the 10% NaOH solution was added and was mixed for 15 minutes. Water for injection sufficient to raise the volume to 25 ml was then added and the resulting solution was mixed for 2 minutes and filtered through a 0.2 micron PES filter.

Example 2

The procedures of Example 1 were followed, with the exception that ethanol was not added and the batch size was 600 ml.

The bulk solutions of both the examples were analyzed and the results are shown in Table 1 below:

TABLE 1

| | Example 1 With additional Ethanol | Example 2 Without additional Ethanol |
| --- | --- | --- |
| Phenobarbital base | Less than 5000 ppm ethanol | |
| Initial analysis | 0M | 0M |
| Total Impurity (%) | 0.06 | 0.314 |

Table 1 illustrates that the impurity profile in the composition with additional ethanol (example 1) is better than the composition without ethanol (example 2). It is to be noted that the phenobarbital base API as used in these examples had an ethanol content of less than 5000 ppm. Thus, the composition of example 1, comprises an ethanol content above 5000 ppm. Whereas, the composition of example 2 comprises no additional ethanol and thus the amount of ethanol in the composition of example 2 is equal to the amount present in phenobarbital base API (less than 5000 ppm) or less.

Example 3

In a clean and dry vessel, 3.64 g phenobarbital base and water for injection were mixed by stirring until the phenobarbital base was dissolved. 6.3 ml of an aqueous 10% NaOH solution was then added while stirring. Water for injection was then added to bring the volume up to 100 ml and the resulting mixture was stirred for 2 minutes.

Example 4

The procedures of Example 3 were followed, with the exception that following the step of dissolving phenobarbital in water for injection, 6.3 mL of 96% ethanol was added to the mixture. As with Example 3, 6.3 mL of an aqueous 10% NaOH solution was then added while stirring. Water for injection was then added to bring the volume up to 100 ml and the resulting mixture was stirred for 2 minutes.

The results for Examples 3 and 4 are shown in Table 2 below:

TABLE 2

| | Example 3 Without additional ethanol | | Example 4 With additional ethanol | |
| --- | --- | --- | --- | --- |
| Phenobarbital base | Less than 5000 ppm ethanol | | | |
| | Total Impurities (%) | | | |
| Stage of Analysis | 2-8° C. | 20-25° C. | 2-8° C. | 20-25° C. |
| 0 hr | 0.386 | 0.386 | 0.344 | 0.344 |
| 8 hr | 0.969 | 2.526 | 0.735 | 1.93 |
| 24 hr | 5.065 | 7.423 | 3.982 | 5.586 |

Table 2 illustrates that adding ethanol to the phenobarbital composition in the amounts tested above provided for fewer impurities than the composition that did not have additional ethanol. Ethanol content of 5000 ppm is not sufficient to prevent formation of impurities. The composition wherein additional ethanol was added, afforded a product with improved stability. Degradation of such composition when subjected to stability testing was found to be significantly lower than the composition wherein there was no additional ethanol addition.

Example 5

In a clean and dry vessel, 4 g of phenobarbital sodium was dissolved via stirring in water for injection. 6.3 ml of 96% ethanol was added to the solution while stirring, and water for injection was then added in an amount sufficient to raise the volume to 100 ml. The resulting solution was stirred for 2 minutes.

Example 6

The procedures of Example 5 were reproduced, with the exception that the pH of the final solution was adjusted to 9.0 by using 0.1N HCl.

Example 7

The procedures of Example 5 were reproduced, with the exception that the ethanol was not added.

Example 8

The procedures of Example 6 were reproduced, with the exception that the ethanol was not added It is to be noted that the phenobarbital sodium API as used in these examples had an ethanol content of about 66000 ppm.

The results of Examples 5-8 are shown in Table 3 below:

TABLE 3

| | Composition with Phenobarbital Sodium | | | |
| --- | --- | --- | --- | --- |
| | Example 5 | Example 6 | Example 7 | Example 8 |
| Phenobarbital Na | About 66000 ppm ethanol | | | |
| | 40 mg | 40 mg | 40 mg | 40 mg |
| Ethanol 96% | 0.063 ml | 0.063 ml | — | — |
| pH of Solution | 9.78 | 9.02 | 9.61 | 9.04 |

TABLE 3-continued

| Total Impurities (%) (2-8° C.) | | | | |
|---|---|---|---|---|
| 0 h | 0.004 | 0.005 | 0.007 | 0.005 |
| 1 h | 0.012 | 0.011 | 0.016 | 0.011 |
| 2 h | 0.025 | 0.014 | 0.028 | 0.017 |
| 4 h | 0.026 | 0.017 | 0.031 | 0.018 |
| 8 h | 0.028 | 0.016 | 0.032 | 0.02 |
| 24 h | 0.04 | 0.015 | 0.052 | 0.022 |

Table 3 shows that when the amount of ethanol present in phenobarbital sodium composition was above 5000 ppm then the formation of total impurities was minimized.

Example 9

In a clean and dry vessel, 60 g of phenobarbital sodium was dissolved via stirring in 1000 ml water for injection and further added 94.5 mL of 96% ethanol. The clarity of the solution was reviewed to ensure that it was clear, and then water for injection sufficient to raise the volume to 1500 ml was added and the solution was stirred followed by filtered through a 0.2 micron PES filter and lyophilization. The lyophilized phenobarbital sodium was kept on stability at 2-8° C. for 36 months. The lyophilized phenobarbital sodium was analyzed for ethanol content at regular intervals.

Example 10

The procedures of Example 9 were reproduced, with the exception that the pH was adjusted to 9 by the use of 5% HCl and then lyophilized. The lyophilized phenobarbital sodium was kept on stability at 2-8° C. for 36 months. The lyophilized phenobarbital sodium was analyzed for ethanol content at regular intervals.

It is to be noted that the phenobarbital sodium API as used in these examples had an ethanol content of about 66000 ppm.

The results of Examples 9 and 10 are shown in Table 4 below:

TABLE 4

| | Example 9 | Example 10 |
|---|---|---|
| Initial | 38474.7 | 53078.7 |
| 1M | 52188.3 | 66539.3 |
| 3M | 46489.6 | 54457 |
| 6M | 34028.5 | 49584.1 |
| 12M | 37039.5 | 45440 |
| 18M | 42227.5 | 53834.1 |

TABLE 4-continued

| | Example 9 | Example 10 |
|---|---|---|
| 24M | 38035 | 46805 |
| 36M | 45139 | 52043 |

Table 4 shows that when additional ethanol is added in the compositions followed by lyophilizing the solution, the amount of ethanol present in the tested compositions were within the range of from about 34000 ppm to about 66000 ppm.

Example 11

In a clean and dry vessel, 64 g of phenobarbital sodium was dissolved via stirring in 1200 ml water for injection and the clarity of the solution was observed to ensure that it was clear. Water for injection was then added to the solution in an amount sufficient to raise the volume to 1600 ml and the solution was stirred, filtered through a 0.2 micron PES filter and lyophilized. The lyophilized phenobarbital sodium was kept on stability at 20-25° C. for 36 months. The lyophilized phenobarbital sodium was analyzed for ethanol content at regular intervals.

Example 12

The procedures of Example 11 were reproduced, with the exception that the batch size was 1800 ml. The lyophilized phenobarbital sodium was kept on stability at 20-25° C. for 36 months. The lyophilized phenobarbital sodium was analyzed for ethanol content at regular intervals.

It is to be noted that the phenobarbital sodium API as used in these examples had an ethanol content of about 66000 ppm.

The results of Examples 11 and 12 were are shown in Table 5 below:

TABLE 5

| | Example 11 | | Example 12 | | West-ward's Composition* |
|---|---|---|---|---|---|
| Phenobarbital sodium | About 66000 ppm ethanol | | | | |
| Ethanol | — | | | | 0.1 ml/ml |
| Stage of Analysis | 24M | 36M | 24M | 36M | analysis after 2.1 year |
| Solvents (Ethanol in ppm) | 18802 | 16680 | 17030 | 13826 | 66436.1 |
| Unknown Impurities (Highest Unspecified) (%) | 0.057 | 0.029 | 0.019 | 0.033 | 2.113 |
| Total Impurities (%) | 0.138 | 0.047 | 0.039 | 0.067 | 2.187 |
| Osmolality (mOsm/kg) | 370 | 371 | 361 | 357 | 1341 |

*West-ward's composition is Phenobarbital sodium in ethanol, benzyl alcohol and propylene glycol Table 5 illustrates that despite the use of a higher level of ethanol in a West-ward's product of phenobarbital sodium at 65 mg/ml, the impurities formation therein is higher than the pharmaceutical composition of preferred embodiments of the present disclosure. Accordingly, the optimum amount of ethanol and lyophilization may be achieved so as to provide for the greatest control of impurities in the composition.

During storage, the amount of ethanol present in the composition may decrease to about 12000 ppm, and thus composition containing ethanol in a range of 12000 to 66000 ppm provide for controlled and lowered levels of impurities. The products of example 11 and 12 were subjected to stability testing. The results of the stability tests are shown in Table 6 below:

TABLE 6

|  | Example 11 | Example 12 |
|---|---|---|
| Initial | 24333 | 15510.7 |
| 1M | 18321 | 15639.7 |
| 3M | 22172.2 | 15540 |
| 6M | 23154.3 | 15034 |
| 12M | 22891 | 15018 |
| 18M | 18496 | 12307 |
| 24M | 18802 | 17030 |
| 36M | 16680 | 13826 |

Table 6 shows that the amount of ethanol present in the tested compositions was within the range of about 12000 ppm to about 25000 ppm.

Examples 13 & 14

In a clean and dry vessel, ~50 L of water for injection was added and maintained at 2-8° C. Nitrogen purging was performed for 30 min. ~2.0 kg of phenobarbital sodium was dissolved via stirring for 5-10 min. in to the water for injection and the clarity of the solution was observed to ensure that it was clear. Solution was filtered through a 0.2 micron PES filter and lyophilized. Ethanol content in the lyophilized phenobarbital sodium was measured to be about 13114 ppm. The lyophilized phenobarbital sodium was kept on stability at 20-25° C. for 36 months. Manufactured batch was also evaluated for reconstitution (in-use) stability. Drug product was reconstituted in 0.9% sodium chloride injection and stored at 20-25° C. and 2-8° C. for its stability evaluation. Reconstituted solution was analyzed at predefined time intervals.

It is to be noted that the phenobarbital sodium API as used in these examples had an ethanol content of about 70000 ppm.

The results of examples 13 were as shown in Table 7 below:

TABLE 7

| Storage | 20-25° C. | | | | 2-8° C. | | | |
|---|---|---|---|---|---|---|---|---|
| Stage of analysis | 0 h | 4 h | 8 h | 12 h | 0 h | 12 h | 24 h | 36 h |
| Unknown impurity (highest unspecified) (%) | BQL | BQL | 0.053 | 0.101 | BQL | 0.072 | BQL | BQL |
| Total impurity (%) | BQL | BQL | 0.053 | 0.101 | BQL | 0.072 | BQL | BQL |
| Osmolality mOsm/kg | 365 | 371 | 366 | 366 | 371 | 366 | 364 | 368 |

BQL: Below Quantitation Limit (0.05%)

The results of examples 14 were as shown in Table 8 below:

TABLE 8

| Storage | 20-25° C. | | | | 2-8° C. | | | |
|---|---|---|---|---|---|---|---|---|
| Stage of analysis | 0 h | 4 h | 8 h | 12 h | 0 h | 12 h | 24 h | 36 h |
| Unknown impurity (highest unspecified) (%) | BQL | BQL | BQL | 0.088 | BQL | 0.063 | BQL | BQL |
| Total impurity (%) | BQL | BQL | BQL | 0.088 | BQL | 0.063 | BQL | BQL |
| Osmolality mOsm/kg | 367 | 369 | 369 | 365 | 367 | 367 | 369 | 365 |

BQL: Below Quantitation Limit (0.05%)

Examples 15 and 16

Two 10% NaOH solutions were prepared in 50 ml flasks by mixing 5 g NaOH with water for injection sufficient to make 30 ml of solution. The resulting solution was mixed and shaken well.

To prepare a bulk solution containing alcohol (example 15), 36.4 mg phenobarbital was placed in a clean and dry vessel. 0.045 ml of a 96% ethanol was added and the resultant was shaken and subject to a vortex for 1 minute. To this solution 0.063 ml of a 10% NaOH solution prepared previously was added and the resultant was subject to a vortex for 15 minutes. Water for injection sufficient to make 1 ml solution was then added and the resultant was subject to a vortex for 10 minutes. The resulting solution was transferred to a measuring cylinder and the pH was checked and adjusted by 0.1N HCl to be 9.78. Water for injection was added to obtain 1 ml of solution and the solution was stirred for 2 minutes. The resulting solution was filtered through a 0.2 micron PES filter, and the filtrate was collected and kept at room temperature (20-25° C.) or 2-8° C. until analysis.

To prepare a bulk solution free from alcohol (example 16), 36.4 mg phenobarbital was placed in a clean and dry vessel. 0.045 ml of a 10% NaOH solution prepared previously was added and the resultant was subject to a vortex for 15 minutes. Water for injection sufficient to make 1 ml solution was then added and the resultant was subject to a vortex for 10 minutes. The resulting solution was transferred to a measuring cylinder and the pH was checked and adjusted by 0.1N HCl to be 9.74. Water for injection was added to obtain 1 ml of solution and the solution was stirred for 2 minutes. The resulting solution was filtered through a 0.2 micron PES filter, and the filtrate was collected and kept at room temperature (20-25° C.) or 2-8° C. until analysis.

The two bulk solutions were analyzed at set time periods and Table 9 shows the results.

TABLE 9

| | Impurity | 20-25° C. | | | | 2-8° C. | | |
|---|---|---|---|---|---|---|---|---|
| | | 0 h | 12 h | 24 h | 36 h | 0 h | 24 h | 36 h |
| Example 15 | Unknown impurity (highest unspecified) (%) | 0.042 | 0.371 | 0.708 | 1.002 | 0.042 | 0.151 | 0.219 |
| | Total Impurity (%) | 0.064 | 0.398 | 0.764 | 1.091 | 0.064 | 0.173 | 0.236 |
| Example 16 | Unknown impurity (highest unspecified) (%) | 0.065 | 0.634 | 1.207 | 1.724 | 0.065 | 0.269 | 0.384 |
| | Total Impurity(%) | 0.078 | 0.674 | 1.288 | 1.859 | 0.078 | 0.293 | 0.404 |

Even though certain specific embodiments are thoroughly described in the present application, it should be understood that the same concepts disclosed with respect to those specific embodiments are also applicable to other embodiments. Furthermore, individual elements of the compositions and methods disclosed herein are described with reference to particular embodiments only for the sake of convenience. It should be understood that individual elements of the compositions and methods disclosed herein are applicable to embodiments other than the specific embodiments in which they are described.

In addition, it should be understood that the scope of the present disclosure is not limited to the above-described embodiments, and those skilled in the art will appreciate that various modifications and alterations are possible without departing from the scope of the present disclosure. For example, the batch sizes may be altered by a person having ordinary skill in the art while staying within the present disclosure.

Features of the Invention

A1. A pharmaceutical composition of phenobarbital or salts thereof that has been reconstituted from a lyophilized pharmaceutical composition of phenobarbital or salts thereof, wherein the amount of total impurities in the pharmaceutical composition does not exceed 0.2% following 12 hours of storage at 20-25° C. or 36 hours of storage at 2-8° C.

A2. The pharmaceutical composition of feature A1, wherein the pharmaceutical composition has an alcohol content in the range from about 5000 ppm to about 66000 ppm or alternatively from about 5000 ppm to about 70000 ppm.

A3. The pharmaceutical composition of feature A1, wherein the pharmaceutical composition has an alcohol content is in the range from about 12000 ppm to about 66000 ppm.

A4. The pharmaceutical composition of feature A1, wherein the pharmaceutical composition has an alcohol content is in the range from about 12000 ppm to about 25000 ppm.

A5. The pharmaceutical composition of features A2-4, wherein alcohol is a $C_1$-$C_3$ alcohol, such as ethanol.

A6. The pharmaceutical composition of feature A1, wherein phenobarbital or salts thereof is phenobarbital sodium.

A7. The pharmaceutical composition of feature A1, wherein the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

A8. The pharmaceutical composition of feature A1, wherein the lyophilized pharmaceutical composition is reconstituted with water for injection, an aqueous saline or an aqueous dextrose solution.

A9. The pharmaceutical composition of feature A1, wherein the pharmaceutical composition is an aqueous solution for injection of phenobarbital or salts thereof.

A10. The pharmaceutical composition of feature A1, wherein phenobarbital or salts thereof is present in a concentration of 10-200 mg/ml.

A11. The pharmaceutical composition of feature A1, wherein the pharmaceutical composition is free of benzyl alcohol.

A12. The pharmaceutical composition of feature A1, wherein the pharmaceutical composition is free of propylene glycol.

A13. The pharmaceutical composition of feature A1, wherein the pharmaceutical composition has an osmolality below 500 mOsm/kg.

A14. A method for the treatment of neonatal seizure in newborn infants of 2 weeks of age or younger in need thereof, comprising administering the pharmaceutical composition of phenobarbital or salts thereof that has been reconstituted from a lyophilized pharmaceutical composition of phenobarbital or salts thereof, wherein the amount of total impurities in the pharmaceutical composition does not exceed 0.2% following 12 hours of storage at 20-25° C. or 36 hours of storage at 2-8° C.

A15. The method of feature A14, wherein the pharmaceutical composition is administered intravenously by infusion at a dose of 20 mg/kg over a course of 15 minutes.

A16. The method of feature A14, wherein the method comprises administering the pharmaceutical composition at an initial loading dose of 20 mg/kg over a course of 15 minutes and measuring the electrographic seizures; and if electrographic seizures persist or recur after completion of the initial loading dose, a second dose of 20 mg/kg is administered over subsequent 15 minutes for a total loading dose of 40 mg/kg.

A17. The method of feature A14, wherein the method comprises administering the pharmaceutical composition to neonates in whom correctable abnormalities have been excluded or corrected.

A18. The method of feature A17, wherein the correctable abnormalities are selected from hypoglycemia or hypocalcemia.

A19. The method of feature A14, wherein the pharmaceutical composition has an alcohol content in the range from about 5000 ppm to about 66000 ppm or alternatively from about 5000 ppm to about 70000 ppm.

A20. The method of feature A14, wherein the pharmaceutical composition has an alcohol content is in the range from about 12000 ppm to about 66000 ppm.

A21. The method of feature A14, wherein the pharmaceutical composition has an alcohol content is in the range from about 12000 ppm to about 25000 ppm.

A22. The method of features A19-21, wherein alcohol is a $C_1$-$C_3$ alcohol, such as ethanol.

A23. The method of feature A14, wherein phenobarbital or salts thereof is phenobarbital sodium.

A24. The method of feature A14, wherein the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

A25. The method of feature A14, wherein the lyophilized pharmaceutical composition is reconstituted with water for injection, an aqueous saline or an aqueous dextrose solution.

A26. The method of feature A14, wherein the pharmaceutical composition is an aqueous solution for injection of phenobarbital or salts thereof.

A27. The method of feature A14, wherein phenobarbital or salts thereof is present in a concentration of 10-200 mg/ml.

A28. The method of feature A14, wherein the pharmaceutical composition is free of benzyl alcohol.

A29. The method of feature A14, wherein the pharmaceutical composition is free of propylene glycol.

A30. The method of feature A14, wherein the pharmaceutical composition has an osmolality below 500 mOsm/kg.

A31. A pharmaceutical composition of phenobarbital or salts thereof, wherein the pharmaceutical composition has an alcohol content in the range from about 5000 ppm to about 66000 ppm or alternatively from about 5000 ppm to about 70000 ppm.

A32. The pharmaceutical composition of feature A31, wherein the composition has an alcohol content in the range from about 12000 ppm to about 66000 ppm.

A33. The pharmaceutical composition of feature A31, wherein the composition has an alcohol content in the range from about 12000 ppm to about 25000 ppm.

A34. The pharmaceutical composition of features A31-33, wherein alcohol is a $C_1$-$C_3$ alcohol, such as ethanol.

A35. The pharmaceutical composition of feature A31, wherein phenobarbital or salts thereof is phenobarbital sodium.

A36. The pharmaceutical composition of feature A31, wherein the pharmaceutical composition is a lyophilized pharmaceutical composition of phenobarbital or salts thereof.

A37. The pharmaceutical composition of feature A36, wherein the lyophilized pharmaceutical composition is stable up to 36 months of storage at 20-25° C.

A38. The pharmaceutical composition of feature A37, wherein the amount of total impurities present following 36 months of storage at 20-25° C. does not exceed 0.5%.

A39. The pharmaceutical composition of feature A37, wherein the amount of total impurities present following 36 months of storage at 20-25° C. does not exceed 0.2%.

A40. The pharmaceutical composition of feature A31, wherein the pharmaceutical composition is an aqueous solution for injection of phenobarbital or salts thereof.

A41. The pharmaceutical composition of feature A40, wherein the aqueous solution is reconstituted from the lyophilized pharmaceutical composition of phenobarbital or salts thereof.

A42. The pharmaceutical composition of feature A41, wherein the lyophilized pharmaceutical composition of phenobarbital or salts thereof is reconstituted with water for injection, an aqueous saline or an aqueous dextrose solution.

A43. The pharmaceutical composition of feature A40, wherein phenobarbital or salts thereof is present in a concentration of 10-200 mg/ml.

A44. The pharmaceutical composition of feature A40, wherein the aqueous solution is stable up to 12 hours of storage at 20-25° C.

A45. The pharmaceutical composition of feature A44, wherein the amount of total impurities present following 12 hours of storage at 20-25° C. does not exceed 0.5%.

A46. The pharmaceutical composition of feature A44, wherein the amount of total impurities present following 12 hours of storage at 20-25° C. does not exceed 0.2%.

A47. The pharmaceutical composition of feature A40, wherein the aqueous solution is stable up to 36 hours of storage at 2-8° C.

A48. The pharmaceutical composition of feature A47, wherein the amount of total impurities present following 36 hours of storage at 2-8° C. does not exceed 0.5%.

A49. The pharmaceutical composition of feature A47, wherein the amount of total impurities present following 36 hours of storage at 2-8° C. does not exceed 0.2%.

A50. The pharmaceutical composition of feature A40, wherein the aqueous solution has an osmolality below 500 mOsm/kg.

A51. The pharmaceutical composition of features A38-39, A45-46 and A48-49, wherein the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

A52. The pharmaceutical composition of feature A31, wherein the pharmaceutical composition is free of benzyl alcohol.

A53. The pharmaceutical composition of feature A31, wherein the pharmaceutical composition is free of propylene glycol.

A54. A method for the treatment of neonatal seizure in newborn infants of 2 weeks of age or younger in need thereof, comprising administering the pharmaceutical composition of phenobarbital or salts thereof, wherein the pharmaceutical composition has an alcohol content in the range from about 5000 ppm to about 66000 ppm or alternatively from about 5000 ppm to about 70000 ppm.

A55. The method of feature A54, wherein the pharmaceutical composition is administered intravenously by infusion at a dose of 20 mg/kg over a course of 15 minutes.

A56. The method of feature A54, wherein the method comprises administering the pharmaceutical composition at an initial loading dose of 20 mg/kg over a course of 15 minutes and measuring the electrographic seizures; and if the electrographic seizures persist or recur after completion of the initial loading dose, a second dose 20 mg/kg is administered over the subsequent 15 minutes for a total loading dose of 40 mg/kg.

A57. The method of feature A54, wherein the method comprises administering the pharmaceutical composition to neonates in whom correctable abnormalities have been excluded or corrected.

A58. The method of feature A57, wherein the correctable abnormalities are selected from hypoglycemia or hypocalcemia.

A59. The method of feature A54, wherein the pharmaceutical composition has an alcohol content in the range from about 12000 ppm to about 66000 ppm.

A60. The method of feature A54, wherein the pharmaceutical composition has an alcohol content in the range from about 12000 ppm to about 25000 ppm.

A61. The method of features A54, A59-60, wherein alcohol is a $C_1$-$C_3$ alcohol, such as ethanol.

A62. The method of feature A54, wherein phenobarbital or salts thereof is phenobarbital sodium.

A63. The method of feature A54, wherein the pharmaceutical composition is a lyophilized pharmaceutical composition of phenobarbital or salts thereof.

A64. The method of features A63, wherein the lyophilized pharmaceutical composition is stable up to 36 months of storage at 20-25° C.

A65. The method of features A64, wherein the amount of total impurities present following 36 months of storage at 20-25° C. does not exceed 0.5%.

A66. The method of features A64, wherein the amount of total impurities present following 36 months of storage at 20-25° C. does not exceed 0.2%.

A67. The method of feature A54, wherein the pharmaceutical composition is an aqueous solution for injection of phenobarbital or salts thereof.

A68. The method of features A67, wherein the aqueous solution is reconstituted from the lyophilized pharmaceutical composition of phenobarbital or salts thereof.

A69. The method of features A68, wherein the lyophilized pharmaceutical composition is reconstituted with water for injection, an aqueous saline or an aqueous dextrose solution.

A70. The method of features A67, wherein the aqueous solution is stable up to 12 hours of storage at 20-25° C.

A71. The method of features A70, wherein the amount of total impurities present following 12 hours of storage at 20-25° C. does not exceed 0.2%.

A72. The method of features A67, wherein the aqueous solution is stable up to 36 hours of storage at 2-8° C.

A73. The method of features A72, wherein the amount of total impurities present following 36 hours of storage at 2-8° C. does not exceed 0.2%.

A74. The method of features A67, wherein the aqueous solution has an osmolality below 500 mOsm/kg.

A75. The method of feature A54, wherein the pharmaceutical composition is free of benzyl alcohol.

A76. The method of feature A54, wherein the pharmaceutical composition is free of propylene glycol.

A77. A lyophilized pharmaceutical composition of phenobarbital or salts thereof, wherein the composition has an alcohol content in the range from about 5000 ppm to about 66000 ppm or alternatively from about 5000 ppm to about 70000 ppm.

A78. The lyophilized pharmaceutical composition of feature A77, wherein the lyophilized pharmaceutical composition has an alcohol content in the range from about 12000 ppm to about 66000 ppm.

A79. The lyophilized pharmaceutical composition of feature A77, wherein the lyophilized pharmaceutical composition has an alcohol content in the range from about 12000 ppm to about 25000 ppm.

A80. The lyophilized pharmaceutical composition of features A77-79, wherein alcohol is a $C_1$-$C_3$ alcohol, such as ethanol.

A81. The lyophilized pharmaceutical composition of feature A77, wherein phenobarbital or salts thereof is phenobarbital sodium.

A82. The lyophilized pharmaceutical composition of feature A77 is stable up to 36 months of storage at 20-25° C.

A83. The lyophilized pharmaceutical composition of feature A82, wherein the amount of total impurities present following 36 months of storage at 20-25° C. does not exceed 0.5%.

A84. The lyophilized pharmaceutical composition of feature A82, wherein the amount of total impurities present following 36 months of storage at 20-25° C. does not exceed 0.2%.

A85. The lyophilized pharmaceutical composition of features A83-84, wherein the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

A86. The lyophilized pharmaceutical composition of feature A77, wherein the lyophilized pharmaceutical composition is free of benzyl alcohol.

A87. The lyophilized pharmaceutical composition of feature A77, wherein the lyophilized pharmaceutical composition is free of propylene glycol.

A88. A method for the treatment of neonatal seizure in newborn infants of 2 weeks of age or younger in need thereof, comprising administering the lyophilized pharmaceutical composition of phenobarbital or salts thereof, and wherein the lyophilized pharmaceutical composition has an alcohol content in the range from about 5000 ppm to about 66000 ppm or alternatively from about 5000 ppm to about 70000 ppm.

A89. The method of feature A88 comprises reconstituting the lyophilized pharmaceutical composition of phenobarbital or salts thereof immediately prior to the administration.

A90. The method of feature A89, wherein the lyophilized pharmaceutical composition is reconstituted with water for injection, an aqueous saline or an aqueous dextrose solution to obtain the aqueous solution for injection of phenobarbital or salts thereof.

A91. The method of feature A90, wherein the aqueous solution is administered intravenously by infusion at a dose of 20 mg/kg over a course of 15 minutes.

A92. The method of features A88 and A89, wherein the method comprises administering the aqueous solution at an initial loading dose of 20 mg/kg over a course of 15 minutes and measuring the electrographic seizures; and if the electrographic seizures persist or recur after completion of the initial loading dose, a second dose 20 mg/kg is administered over the subsequent 15 minutes for a total loading dose of 40 mg/kg.

A93. The method of feature A88, wherein the method comprises administering to neonates in whom correctable abnormalities have been excluded or corrected.

A94. The method of feature A93, wherein the correctable abnormalities are selected from hypoglycemia or hypocalcemia.

A95. The method of feature A88, wherein the lyophilized pharmaceutical composition has an alcohol content in the range from about 12000 ppm to about 66000 ppm.

A96. The method of feature A88, wherein the lyophilized pharmaceutical composition has an alcohol content in the range from about 12000 ppm to about 25000 ppm.

A97. The method of features A88, A95-96, wherein alcohol is a $C_1$-$C_3$ alcohol, such as ethanol.

A98. The method of feature A88, wherein phenobarbital or salts thereof is phenobarbital sodium.

A99. The method of feature A88, wherein the lyophilized pharmaceutical composition is stable up to 36 months of storage at 20-25° C.

A100. The method of feature A99, wherein the amount of total impurities present following 36 months of storage at 20-25° C. does not exceed 0.5%.

A101. The method of feature A99, wherein the amount of total impurities present following 36 months of storage at 20-25° C. does not exceed 0.2%.

A102. The method of features A100-101, wherein the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

A103. The method of feature A88, wherein the lyophilized pharmaceutical composition is free of benzyl alcohol.

A104. The method of feature A88, wherein the lyophilized pharmaceutical composition is free of propylene glycol.

A105. A pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or alternatively from about 5000 ppm to about 70000 ppm.

A106. The pharmaceutical composition of feature A105, wherein the pharmaceutical composition has an alcohol content in the range from about 12000 ppm to about 66000 ppm.

A107. The pharmaceutical composition of feature A105, wherein the pharmaceutical composition has an alcohol content in the range from about 12000 ppm to about 25000 ppm.

A108. The pharmaceutical composition of feature A105-107, wherein alcohol is a $C_1$-$C_3$ alcohol, such as ethanol.

A109. The pharmaceutical composition of feature A105, wherein phenobarbital or salts thereof is phenobarbital sodium.

A110. The pharmaceutical composition of feature A105, wherein the lyophilized pharmaceutical composition is reconstituted with water for injection, an aqueous saline or an aqueous dextrose solution.

A111. The pharmaceutical composition of feature A105 is an aqueous solution for injection of phenobarbital or salts thereof.

A112. The pharmaceutical composition of feature A105, wherein phenobarbital or salts thereof is present in a concentration of 10-200 mg/ml.

A113. The pharmaceutical composition of feature A105, wherein the pharmaceutical composition is stable up to 12 hours of storage at 20-25° C.

A114. The pharmaceutical composition of feature A113, wherein the amount of total impurities present following 12 hours of storage at 20-25° C. does not exceed 0.5%.

A115. The pharmaceutical composition of feature A113, wherein the amount of total impurities present following 12 hours of storage at 20-25° C. does not exceed 0.2%.

A116. The pharmaceutical composition of feature A105, wherein the pharmaceutical composition is stable up to 36 hours of storage at 2-8° C.

A117. The pharmaceutical composition of feature A116, wherein the amount of total impurities present following 36 hours of storage at 2-8° C. does not exceed 0.5%.

A118. The pharmaceutical composition of feature A116, wherein the amount of total impurities present following 36 hours of storage at 2-8° C. does not exceed 0.2%.

A119. The pharmaceutical composition of features A114-115 and A117-118, wherein the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

A120. The pharmaceutical composition of feature A105, wherein the pharmaceutical composition has an osmolality below 500 mOsm/kg.

A121. The pharmaceutical composition of feature A105, wherein the pharmaceutical composition is free of benzyl alcohol.

A122. The pharmaceutical composition of feature AA105, wherein the pharmaceutical composition is free of propylene glycol.

A123. A method for the treatment of neonatal seizure in newborn infants of 2 weeks of age or younger in need thereof, comprising administering a pharmaceutical composition of phenobarbital or salts thereof that has been reconstituted from a lyophilized pharmaceutical composition of phenobarbital or salts thereof, and wherein the pharmaceutical composition has an alcohol content in the range from about 5000 ppm to about 66000 ppm or alternatively from about 5000 ppm to about 70000 ppm.

A124. The method of feature A123, wherein the pharmaceutical composition is administered intravenously by infusion at a dose of 20 mg/kg over a course of 15 minutes.

A125. The method of feature A123, wherein the method comprises administering the pharmaceutical composition at an initial loading dose of 20 mg/kg over a course of 15 minutes and measuring the electrographic seizures; and if the electrographic seizures persist or recur after completion of the initial loading dose, a second dose 20 mg/kg is administered over the subsequent 15 minutes for a total loading dose of 40 mg/kg.

A126. The method of feature A123, wherein the method comprises administering the pharmaceutical composition to neonates in whom correctable abnormalities have been excluded or corrected.

A127. The method of feature A126, wherein the correctable abnormalities are selected from hypoglycemia or hypocalcemia.

A128. The method of feature A123, wherein the pharmaceutical composition has an alcohol content in the range from about 12000 ppm to about 66000 ppm.

A129. The method of feature A126, wherein the pharmaceutical composition has an alcohol content in the range from about 12000 ppm to about 25000 ppm.

A130. The method of features A123, A128-129, wherein alcohol is a $C_1$-$C_3$ alcohol, such as ethanol.

A131. The method of feature A123, wherein phenobarbital or salts thereof is phenobarbital sodium.

A132. The method of feature A123, wherein the lyophilized pharmaceutical composition is reconstituted with water for injection, an aqueous saline or an aqueous dextrose solution.

A133. The method of feature A123, wherein the pharmaceutical composition is an aqueous solution for injection of phenobarbital or salts thereof.

A134. The method of feature A123, wherein phenobarbital or salts thereof is present in a concentration of 10-200 mg/ml.

A135. The method of feature A123, wherein the pharmaceutical composition is stable up to 12 hours of storage at 20-25° C.

A136. The method of feature A135, wherein the amount of total impurities present following 12 hours of storage at 20-25° C. does not exceed 0.2%.

A137. The method of feature A123, wherein the pharmaceutical composition is stable up to 36 hours of storage at 2-8° C.

A138. The method of feature A137, wherein the amount of total impurities present following 36 hours of storage at 2-8° C. does not exceed 0.2%.

A139. The method of features A136 and A138, wherein the total impurities are selected from 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

A140. The method of feature A123, wherein the pharmaceutical composition has an osmolality below 500 mOsm/kg.

A141. The method of feature A123, wherein the pharmaceutical composition is free of benzyl alcohol.

A142. The method of feature A123, wherein the pharmaceutical composition is free of propylene glycol.

A143. A process of preparing the lyophilized pharmaceutical composition of phenobarbital or salts thereof having an alcohol content in the range from about 5000 ppm to about 66000 ppm or alternatively from about 5000 ppm to about 70000 ppm, wherein the process comprises dissolving phenobarbital or salts thereof in water to obtain an aqueous solution of phenobarbital or salts thereof in a concentration of 10-200 mg/ml and lyophilizing the aqueous solution to obtain lyophilized pharmaceutical composition of phenobarbital or salts thereof.

A144. The process of feature A143, wherein the process comprises measuring the alcohol content of the aqueous solution of phenobarbital or salts thereof and if the alcohol content is below 5000 ppm then the process further comprises a step of adding alcohol to achieve the alcohol content of at least about 5000 ppm.

A145. The process of features A143, wherein the process comprises measuring the alcohol content of the lyophilized pharmaceutical composition of phenobarbital or salts thereof and if the alcohol content is above 66000 ppm or about 70000 ppm (whichever is desired), the process further comprises repeating the lyophilization step multiple times till the alcohol content of the lyophilized pharmaceutical composition is not more than about 66000 ppm or about 70000 ppm.

A146. The process of feature A143 further comprises addition of a pH modifier to the aqueous solution of phenobarbital or salts thereof to achieve a pH in a range of 9-10.5.

A147. The process of feature A143, wherein the lyophilized pharmaceutical composition has an alcohol content in the range from about 12000 ppm to about 66000 ppm.

A148. The process of feature A143, wherein the lyophilized pharmaceutical composition has an alcohol content in the range from about 12000 ppm to about 25000 ppm.

A149. The process of features A143, A147-148, wherein alcohol is a $C_1$-$C_3$ alcohol, such as ethanol.

A150. The process of feature A143, wherein phenobarbital or salts thereof is phenobarbital sodium.

A151. The process of feature A143, wherein the lyophilized pharmaceutical composition is stable up to 36 months of storage at 20-25° C.

A152. The process of feature A151, wherein the amount of total impurities present following 36 months of storage at 20-25° C. does not exceed 0.5%.

A153. The process of feature A151, wherein the amount of total impurities present following 36 months of storage at 20-25° C. does not exceed 0.2%.

A154. The process of features A152-153, wherein the total impurities are selected from 2-phenyl-2-ethyl acetyl urea, 2-phenyl-2-ethyl-malonamide, α-phenyl-butyrylguanidine, 2-phenylbutyric acid and 5-methyl-5-phenylbarbituric acid.

A155. The process of feature A143, wherein the lyophilized pharmaceutical composition is free of benzyl alcohol.

A156. The process of feature A143, wherein the lyophilized pharmaceutical composition is free of propylene glycol.

A157. A process of preparing the lyophilized pharmaceutical composition of phenobarbital or salts thereof having an alcohol content in the range from about 5000 ppm to about 66000 ppm or alternatively from about 5000 ppm to about 70000 ppm, the process comprises dissolving phenobarbital or salts thereof in water to obtain an aqueous solution having a concentration 10-200 mg/ml; measuring the alcohol content of aqueous solution; if the alcohol content is below 5000 ppm, adding alcohol to achieve the alcohol content of at least about 5000 ppm; lyophilizing the aqueous solution to obtain lyophilized pharmaceutical composition; measuring the alcohol content of the lyophilized pharmaceutical composition; if the alcohol content is above about 66000 ppm or above about 70000 ppm (whichever is desired), repeating the lyophilization step multiple times till the alcohol content of the lyophilized pharmaceutical composition is not more than about 66000 ppm or about 70000 ppm.

A158. The process of feature A157 further comprises addition of a pH modifier to the aqueous solution of phenobarbital or salts thereof to achieve a pH in a range of 9-10.5.

A159. The process of feature A157, wherein the lyophilized pharmaceutical composition has an alcohol content in the range from about 12000 ppm to about 66000 ppm.

A160. The process of feature A157, wherein the lyophilized pharmaceutical composition has an alcohol content in the range from about 12000 ppm to about 25000 ppm.

A161. The process of features A157, A159-160, wherein alcohol is a $C_1$-$C_3$ alcohol, such as ethanol.

A162. The process of feature A157, wherein phenobarbital or salts thereof is phenobarbital sodium.

A163. The process of feature A157, wherein the lyophilized pharmaceutical composition is stable up to 36 months of storage at 20-25° C.

A164. The process of feature A163, wherein the amount of total impurities present following 36 months of storage at 20-25° C. does not exceed 0.5%.

A165. The process of feature A163, wherein the amount of total impurities present following 36 months of storage at 20-25° C. does not exceed 0.2%.

A166. The process of features A164-165, wherein the total impurities are selected from 2-phenyl-2-ethyl acetyl urea, 2-phenyl-2-ethyl-malonamide, α-phenyl-butyrylguanidine, 2-phenylbutyric acid and 5-methyl-5-phenylbarbituric acid.

A167. The process of feature A157, wherein the lyophilized pharmaceutical composition is free of benzyl alcohol.

A168. The process of feature A157, wherein the lyophilized pharmaceutical composition is free of propylene glycol.

A169. A process of preparing the pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or alternatively from about 5000 ppm to about 70000 ppm, the process comprises dissolving phenobarbital or salts thereof in water to obtain an aqueous solution having a concentration 10-200 mg/ml; lyophilizing the aqueous solution to obtain lyophilized pharmaceutical composition of phenobarbital or salts thereof; and reconstituting the lyophilized pharmaceutical composition to obtain the pharmaceutical composition of phenobarbital or salts thereof.

A170. The process of feature A169, wherein the process comprises measuring the alcohol content of the aqueous solution of phenobarbital or salts thereof and if the alcohol content is below 5000 ppm then the process further comprises a step of adding alcohol to achieve the alcohol content of at least about 5000 ppm.

A171. The process of features A169, wherein said process comprises measuring the alcohol content of the lyophilized pharmaceutical composition of phenobarbital or salts thereof and if the alcohol content is above about 66000 ppm or about 70000 ppm (whichever is desired), the process further comprises repeating the lyophilization step multiple times till the alcohol content of the lyophilized pharmaceutical composition is not more than about 66000 ppm or about 70000 ppm.

A172. The process of feature A169 further comprises addition of pH modifier to the aqueous solution of phenobarbital or salts thereof to achieve a pH in a range of 9-10.5.

A173. The process of feature A169, wherein the lyophilized pharmaceutical composition is reconstituted with water for injection, an aqueous saline or an aqueous dextrose solution.

A174. The process of feature A169, wherein the pharmaceutical composition is an aqueous solution for injection of phenobarbital or salts thereof.

A175. The process of feature A169, wherein the pharmaceutical composition has an alcohol content in the range from about 12000 ppm to about 66000 ppm.

A176. The process of feature A169, wherein the pharmaceutical composition has an alcohol content in the range from about 12000 ppm to about 25000 ppm.

A177. The process of feature A169, A175-176, wherein alcohol is a $C_1$-$C_3$ alcohol, such as ethanol.

A178. The process of feature A169, wherein phenobarbital or salts thereof is phenobarbital sodium.

A179. The process of feature A169, wherein the pharmaceutical composition is stable up to 12 hours of storage at 20-25° C.

A180. The process of feature A179, wherein the amount of total impurities present following 12 hours of storage at 20-25° C. does not exceed 0.2%.

A181. The process of feature A169, wherein the pharmaceutical composition is stable up to 36 hours of storage at 2-8° C.

A182. The process of feature A181, wherein the amount of total impurities present following 36 hours of storage at 2-8° C. does not exceed 0.2%.

A183. The process of features A180 and A182, wherein the total impurities are selected from 2-phenyl-2-ethyl acetyl urea, 2-phenyl-2-ethyl-malonamide, α-phenyl-butyrylguanidine, 2-phenylbutyric acid and 5-methyl-5-phenylbarbituric acid.

A184. The process of feature A169, wherein the pharmaceutical composition has an osmolality below 500 mOsm/kg.

A185. The process of feature A169, wherein the pharmaceutical composition is free of benzyl alcohol.

A186. The process of feature A169, wherein the pharmaceutical composition is free of propylene glycol.

A187. A process of preparing the pharmaceutical composition of phenobarbital or salts thereof that has been reconstituted from a lyophilized pharmaceutical composition of phenobarbital or salts thereof, wherein the pharmaceutical composition has an alcohol content in the range from about 5000 ppm to about 66000 ppm or alternatively from about 5000 ppm to about 70000 ppm, wherein the process comprises dissolving phenobarbital or salts thereof in water to obtain an aqueous solution having a concentration 10-200 mg/ml; measuring the alcohol content of aqueous solution; if the alcohol content is below 5000 ppm, adding an alcohol to achieve the alcohol content of at least about 5000 ppm; lyophilizing the aqueous solution to obtain lyophilized pharmaceutical composition; measuring the alcohol content of the lyophilized pharmaceutical composition; if the alcohol content is above 66000 ppm, repeating the lyophilization step multiple times till the alcohol content of the lyophilized pharmaceutical composition is not more than about 66000 ppm or not more than 70000 ppm (whichever is desired); and reconstituting the lyophilized pharmaceutical composition to obtain the pharmaceutical composition of phenobarbital or salts thereof.

A188. The process of feature A187 further comprises addition of pH modifier to the aqueous solution of phenobarbital or salts thereof to achieve a pH in a range of 9-10.5.

A189. The process of feature A187, wherein the lyophilized pharmaceutical composition is reconstituted with water for injection, an aqueous saline or an aqueous dextrose solution.

A190. The process of feature A187, wherein the pharmaceutical composition is an aqueous solution for injection of phenobarbital or salts thereof.

A191. The process of feature A187, wherein the pharmaceutical composition has an alcohol content in the range from about 12000 ppm to about 66000 ppm.

A192. The process of feature A187, wherein the pharmaceutical composition has an alcohol content in the range from about 12000 ppm to about 25000 ppm.

A193. The process of feature A187, A191-192, wherein alcohol is a $C_1$-$C_3$ alcohol, such as ethanol.

A194. The process of feature A187, wherein phenobarbital or salts thereof is phenobarbital sodium.

A195. The process of feature A187, wherein the pharmaceutical composition is stable up to 12 hours of storage at 20-25° C.

A196. The process of feature A195, wherein the amount of total impurities present following 12 hours of storage at 20-25° C. does not exceed 0.2%.

A197. The process of feature A187, wherein the pharmaceutical composition is stable up to 36 hours of storage at 2-8° C.

A198. The process of feature A197, wherein the amount of total impurities present following 36 hours of storage at 2-8° C. does not exceed 0.2%.

A199. The process of features A196 and A198, wherein the total impurities are selected from 2-phenyl-2-ethyl acetyl urea, 2-phenyl-2-ethyl-malonamide, α-phenyl-butyrylguanidine, 2-phenylbutyric acid and 5-methyl-5-phenylbarbituric acid.

A200. The process of feature A187, wherein the pharmaceutical composition has an osmolality below 500 mOsm/kg.

A201. The process of feature A187, wherein the pharmaceutical composition is free of benzyl alcohol.

A202. The process of feature A187, wherein the pharmaceutical composition is free of propylene glycol.

A203. A lyophilized pharmaceutical composition of phenobarbital or salts thereof having an alcohol content in the range from about 5000 ppm to about 66000 ppm, wherein the lyophilized pharmaceutical composition is obtained by a process comprising: dissolving phenobarbital or salts thereof in water to obtain an aqueous solution having a concentration 10-200 mg/ml and lyophilizing the aqueous solution to obtain lyophilized pharmaceutical composition of phenobarbital or salts thereof.

A204. A pharmaceutical composition of phenobarbital or salts thereof that has been reconstituted from a lyophilized pharmaceutical composition of phenobarbital or salts thereof having an alcohol content in the range from about 5000 ppm to about 66000 ppm, wherein the pharmaceutical composition is obtained by a process comprising: dissolving phenobarbital or salts thereof in water to obtain an aqueous solution having a concentration 10-200 mg/ml; lyophilizing the aqueous solution to obtain lyophilized pharmaceutical composition of phenobarbital or salts thereof; and reconstituting the lyophilized pharmaceutical composition to obtain the pharmaceutical composition of phenobarbital or salts thereof.

A205. A lyophilized pharmaceutical composition comprising phenobarbital sodium and ethanol, wherein ethanol is present in an amount sufficient to inhibit degradation of phenobarbital sodium, such that the amount of total impurities present following 36 months of storage at 20-25° C. does not exceed 0.2%;
wherein the amount of ethanol sufficient to inhibit degradation of phenobarbital sodium is in the range from about 12000 ppm to about 25000 ppm;
and wherein the pharmaceutical composition is free of benzyl alcohol and propylene glycol.

A206. An aqueous solution for injection comprising phenobarbital sodium and ethanol, wherein ethanol is present in an amount sufficient to inhibit degradation of phenobarbital sodium, such that the amount of total impurities present following 12 hours of storage at 20-25° C. or following 36 hours of storage at 2-8° C. does not exceed 0.2%;
wherein the amount of ethanol sufficient to inhibit degradation of phenobarbital sodium is in the range from about 12000 ppm to about 25000 ppm;
wherein phenobarbital sodium is present in a concentration from 10-200 mg/ml;
wherein the aqueous solution is reconstituted from the lyophilized pharmaceutical composition of phenobarbital sodium;
and wherein the aqueous solution is free of benzyl alcohol and propylene glycol.

A207. A process for the preparation of the pharmaceutical composition of phenobarbital or salts thereof, the process comprises dissolving phenobarbital or salt thereof in water to obtain an aqueous solution having a concentration 10-200 mg/ml and lyophilizing the aqueous solution to obtain lyophilized pharmaceutical composition, wherein phenobarbital or salts thereof has an alcohol content in the range from about 5000 ppm to about 66000 ppm.

A208. A lyophilized pharmaceutical composition of phenobarbital sodium, wherein the composition has an ethanol content in the range from about 12000 ppm to about 25000 ppm; wherein the composition is stable up to 36 months of storage at 20-25° C. such that the amount of total impurities present following 36 months of storage at 20-25° C. does not exceed 0.2%; and wherein the composition is free of benzyl alcohol and propylene glycol.

A209. An aqueous solution for injection of phenobarbital sodium, wherein the aqueous solution has an ethanol content in the range from about 12000 ppm to about 25000 ppm; wherein the aqueous solution is stable up to 12 hours of storage at 20-25° C. or 36 hours of storage at 2-8° C. such that the amount of total impurities present following 12 hours of storage at 20-25° C. or following 36 hours of storage at 2-8° C. does not exceed 0.2%; wherein the aqueous solution is reconstituted from the lyophilized pharmaceutical composition of phenobarbital sodium; and wherein the aqueous solution is free of benzyl alcohol and propylene glycol.

What is claimed is:

1. A lyophilized pharmaceutical composition of phenobarbital or salts thereof having an ethanol content in the range from 12000 ppm to 50000 ppm, wherein an amount of total impurities in the lyophilized pharmaceutical composition does not exceed 0.2% following 36 months of storage at 20-25° C., wherein the lyophilized pharmaceutical composition is free of benzyl alcohol and propylene glycol.

2. The lyophilized pharmaceutical composition of claim 1, wherein the composition has an ethanol content in the range from about 12000 ppm to about 25000 ppm.

3. The lyophilized pharmaceutical composition of claim 1, wherein the phenobarbital or salts thereof is phenobarbital sodium.

4. The lyophilized pharmaceutical composition of claim 1, wherein the total impurities are selected from the group consisting of 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

5. A method for the treatment of neonatal seizure in newborn infants of 2 weeks of age or younger in need thereof, comprising administering the lyophilized pharmaceutical composition of claim 1.

6. The method of claim 5, wherein the method comprises reconstituting the lyophilized pharmaceutical composition immediately prior to the administration.

7. The method of claim 6, wherein the lyophilized pharmaceutical composition is reconstituted with water for injection, an aqueous saline or an aqueous dextrose solution.

8. A lyophilized pharmaceutical composition comprising phenobarbital sodium having an ethanol content in the range from about 12000 ppm to about 25000 ppm, wherein an amount of total impurities in the lyophilized pharmaceutical composition does not exceed 0.2% following 36 months of storage at 20-25° C., and wherein the pharmaceutical composition is free of benzyl alcohol and propylene glycol.

9. A method for the treatment of neonatal seizure in newborn infants of 2 weeks of age or younger in need thereof, comprising administering the lyophilized pharmaceutical composition of claim 8.

10. The method of claim 9, wherein the method comprises reconstituting the lyophilized pharmaceutical composition immediately prior to the administration.

11. The method of claim 10, wherein the lyophilized pharmaceutical composition is reconstituted with water for injection, an aqueous saline or an aqueous dextrose solution.

12. A pharmaceutical composition of phenobarbital or salts thereof made by a method comprising reconstituting a lyophilized pharmaceutical composition of the phenobarbital or salts thereof,
wherein an amount of total impurities in the pharmaceutical composition does not exceed 0.2% following 12 hours of storage at 20-25° C. or 36 hours of storage at 2-8° C., and
wherein the pharmaceutical composition has an ethanol content in a range from 12000 ppm to 50000 ppm.

13. The pharmaceutical composition of claim 12, wherein the ethanol content is in a range of from about 12000 ppm to about 25000 ppm.

14. The pharmaceutical composition of claim 12, wherein the phenobarbital or salts thereof is phenobarbital sodium.

15. The pharmaceutical composition of claim 12, wherein the total impurities are selected from the group consisting of 2-phenyl-2-ethyl acetyl urea, 2-phenyl-2-ethyl-malonamide, α-phenylbutyrylguanidine, 2-phenylbutyric acid and 5-methyl-5-phenylbarbituric acid.

16. The pharmaceutical composition of claim 12, wherein the lyophilized pharmaceutical composition is reconstituted with water for injection, an aqueous saline or an aqueous dextrose solution.

17. The pharmaceutical composition of claim 12, wherein the phenobarbital or salts thereof is present in a concentration of 10-200 mg/ml.

18. The pharmaceutical composition of claim 12, wherein the composition is free of benzyl alcohol and propylene glycol.

19. The pharmaceutical composition of claim 12, wherein the pharmaceutical composition has an osmolality below 500 mOsm/kg.

20. A method for the treatment of neonatal seizure in newborn infants of 2 weeks of age or younger in need thereof, comprising administering a pharmaceutical composition of claim 12.

21. A pharmaceutical composition of phenobarbital sodium having an ethanol content in the range from about 12000 ppm to about 25000 ppm, wherein the pharmaceutical composition is made by reconstituting the lyophilized pharmaceutical composition of phenobarbital sodium;
   wherein the amount of total impurities present following 12 hours of storage at 20-25° C. or following 36 hours of storage at 2-8° C. does not exceed 0.2%;
   wherein phenobarbital sodium is present in a concentration from 10-200 mg/ml; and
   wherein the pharmaceutical composition is free of benzyl alcohol and propylene glycol.

22. The pharmaceutical composition of claim 21, wherein the lyophilized pharmaceutical composition is reconstituted with water for injection, an aqueous saline or an aqueous dextrose solution.

23. A method for the treatment of neonatal seizure in newborn infants of 2 weeks of age or younger in need thereof, comprising administering a pharmaceutical composition of claim 21.

24. The lyophilized pharmaceutical composition of claim 1, wherein the lyophilized pharmaceutical composition comprises HCl.

25. A lyophilized pharmaceutical composition of phenobarbital or salts thereof having an ethanol content in the range from 12000 ppm to 50000 ppm, wherein an amount of total impurities in the lyophilized pharmaceutical composition does not exceed 0.2% following 36 months of storage at 20° C.-25° C.,
   wherein, said lyophilized pharmaceutical composition upon reconstitution with water for injection or an aqueous saline or an aqueous dextrose solution provides a stable reconstituted composition up to 12 hours of storage at 20° C.-25° C. or 36 hours of storage at 2° C.-8° C.;
   wherein, an amount of total impurities in the reconstituted composition does not exceed 0.2% following 12 hours of storage at 20° C.-25° C. or 36 hours of storage at 2° C.-8° C.;
   wherein said lyophilized pharmaceutical composition and said reconstituted composition are free of benzyl alcohol and propylene glycol;
   optionally wherein said lyophilized pharmaceutical composition and said reconstituted composition comprise HCl; and
   wherein said reconstituted composition is suitable for the treatment of neonatal seizure in newborn infants of 2 weeks of age or younger in need thereof.

* * * * *